(12) United States Patent
Coleman et al.

(10) Patent No.: US 10,989,645 B2
(45) Date of Patent: Apr. 27, 2021

(54) NON-INVASIVE PARTICLE SENSOR USING A MULTI-FIBER CONNECTOR

(71) Applicant: ABER INSTRUMNETS, INC., Alexandria, VA (US)

(72) Inventors: Gerald P. Coleman, Marysville, CA (US); Martin P. Debreczeny, Berkeley, CA (US); Jaime Romero, Concord, CA (US)

(73) Assignee: ABER INSTRUMENTS, INC., Arlington, VA (US)

( * ) Notice: Subject to any disclaimer, the term of this patent is extended or adjusted under 35 U.S.C. 154(b) by 0 days.

(21) Appl. No.: 16/537,555

(22) Filed: Aug. 10, 2019

(65) Prior Publication Data

US 2020/0049608 A1 Feb. 13, 2020

Related U.S. Application Data

(60) Provisional application No. 62/717,820, filed on Aug. 11, 2018.

(51) Int. Cl.
*G01N 15/06* (2006.01)
*G01N 33/483* (2006.01)

(52) U.S. Cl.
CPC ......... *G01N 15/06* (2013.01); *G01N 33/4833* (2013.01); *G01N 2015/0693* (2013.01)

(58) Field of Classification Search
CPC ............... G01N 15/06; G01N 33/4833; G01N 2015/0693
USPC .......................................................... 356/338
See application file for complete search history.

(56) References Cited

U.S. PATENT DOCUMENTS

| 5,175,438 | A | * | 12/1992 | Ikeda | B01J 47/04 250/226 |
| 5,483,080 | A | * | 1/1996 | Tam | G01N 21/51 250/574 |
| 6,052,184 | A | * | 4/2000 | Reed | G01N 15/0211 356/337 |
| 6,573,991 | B1 | * | 6/2003 | Debreczeny | G01N 15/0211 356/336 |
| 7,100,462 | B2 | | 9/2006 | Gronvall | |
| 7,339,671 | B2 | | 3/2008 | Peng | |
| 8,405,033 | B2 | | 3/2013 | Debreczeny | |
| 8,603,772 | B2 | | 12/2013 | Debreczeny | |
| 9,738,864 | B2 | * | 8/2017 | Colin | C12M 41/06 |

(Continued)

FOREIGN PATENT DOCUMENTS

| DE | 19611931 | 10/1997 |
| WO | WO 2018/096143 | 5/2018 |

OTHER PUBLICATIONS

Olsson, L.; "On-line and in situ Monitoring of Biomass in Submerged Cultures"; TIBTech (1997) 15: 517-522.

(Continued)

*Primary Examiner* — Roy M Punnoose
(74) *Attorney, Agent, or Firm* — Dinsmore & Shohl LLP

(57) ABSTRACT

This invention provides, e.g., devices for detection of particle concentrations in a vessel in real time from outside the vessel. The device is attached to the vessel so that light from an optic fiber enters a media of the vessel, is scattered by the particles, and the scattered light received by a second optic fiber. The received light is transmitted to a detector, generating a signal to a processor for determination of a particle concentration.

20 Claims, 22 Drawing Sheets

(56) References Cited

U.S. PATENT DOCUMENTS

| | | |
|---|---|---|
| 9,752,974 B2 | 9/2017 | Debreczeny |
| 10,054,532 B2 | 8/2018 | Debreczeny |
| 2011/0206324 A1* | 8/2011 | Childers .............. G02B 6/4277 385/55 |

OTHER PUBLICATIONS

Landgrebe; "On-line Infrared Spectroscopy for Bioprocess Monitoring" Appl Microbiol Biotechnol (2010) 88:11-22.
GE; "Noninvasive Spectroscopy for Monitoring Cell Density in a Fermentation Process" Analytical Chemistry (1994) 66:1354-1362.
Zabriskie, D; "Estimation of Fermentation Biomass Concentration by Measuring Culture Fluorescence" Appl Environ Microbiol (1978) 35: 337-343.
Ude; "Application of an Online-Biomass Sensor in an Optical Multisensory Platform Prototype for Growth Monitoring of Biotechnical Relevant Microorganism and Cell Lines in Single-Use Shake Flasks" Sensors (2014) 14: 17390-17405.
Schmidt-Hager; "Noninvasive Online Biomass Detector System for Cultivation in Shake Flasks" Eng Life Sci (2014) 14: 467-476.
Kensy; "Validation of a High-Throughput Fermentation System Based on Online Monitoring of Biomass and Fluorescence in Continuously Shaken Microtiter Plates" Microbial Cell Factories (2009) 8:31.
Zimmerman, H; "Evaluation of the Applicability of Backscattered Light Measurements to the Determination of Microbial Cell Densities in Microtiter Plates" Anal Bioanal Chem (2006) 386: 2245-2247.

\* cited by examiner

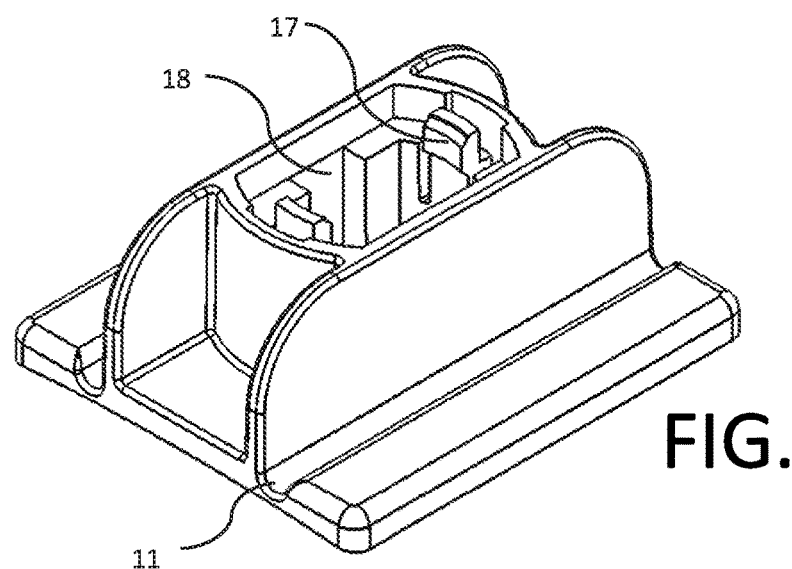
FIG. 6A
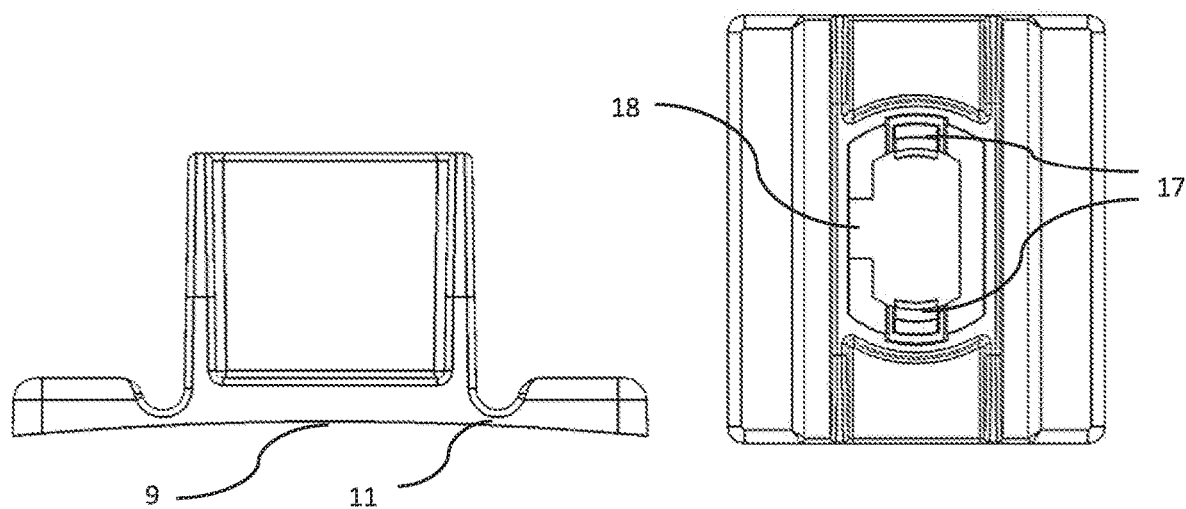
FIG. 6B
FIG. 6C

NON-INVASIVE PARTICLE SENSOR USING A MULTI-FIBER CONNECTOR

CROSS-REFERENCE TO RELATED APPLICATIONS

This application is related to, and claims benefit of, U.S. Provisional Patent Application Ser. No. 62/717,820 filed Aug. 11, 2018, the disclosure of which is incorporated herein by reference in its entirety for all purposes.

FIELD OF THE INVENTION

Methods and devices for non-invasively measuring particulate concentrations in a suspension, e.g. biomass in a liquid cell culture, through the wall of a vessel containing the suspension, using a multi-fiber connector as the sensor. Measurements of particle concentration are made, e.g., by detection of near infrared (NIR) back-scattered light.

BACKGROUND OF THE INVENTION

Measurement of particle concentrations is important in many industrial and research applications. For example, monitoring cell density (e.g. biomass) in liquid cell cultures is used: to determine the growth phase or rate; as a feedback signal for adjusting growth conditions (e.g. dissolved oxygen, pH, media constituents); as an indicator of when to induce expression of genes, harvest cells, or inoculate cells into a larger media volume; and/or as a feedback signal for maintaining a constant biomass during a continuous fermentation (e.g. turbidostat) process. The growth rate of many cultures, particularly microbial organisms (e.g. yeast, bacteria), is limited by the concentration of dissolved oxygen in the medium. The culture of such organisms is often performed in vessels (e.g. fermenters, bioreactors) in which gases are bubbled ("sparged") and the medium is stirred or otherwise agitated, often at such high rates that the bubbles constitute a significant fraction ("gas hold-up") of the total volume. The presence of such a high concentration of bubbles presents a challenge to many techniques for cell growth monitoring.

Many biomass monitoring techniques take advantage of the scattering of light by cells. For example, one of the most common laboratory techniques for monitoring cell growth is to extract a sample, dilute it, and measure its absorbance (e.g. at 600 nm) in a fixed path length (e.g. 1 cm) cell in a spectrophotometer. Absorbance is typically limited to about 0.5 in order to remain in the linear range of Beer's Law. The measured absorbance multiplied by the dilution factor is referred to as the optical density (e.g. "OD 600 nm"), and used as an indication of biomass. Despite its prevalence, this technique has numerous limitations: it requires opening the culture, with the attendant risk of contamination; the dilution step is subject to volumetric error; the extracted sample is expended, of particular concern in small volume cultures; and it is labor-intensive.

In an effort to overcome these limitations and provide continuous ("on-line") monitoring, much work has gone into the development of invasive sensors for measuring optical density directly in the cell culture. Unfortunately, such sensors are often subject to the same limitation of narrow linear range as are off-line techniques: in order to measure biomass over a wide range, the use of multiple sensors, having different optical transmission path lengths, is frequently required. Immersible sensors that measure back-reflected light (instead of transmission) typically have a somewhat wider but still limited linear range of response to biomass, and may suffer, particularly in the low biomass range, from a sensitivity to reflections from nearby non-biological objects within the vessel, such as impellers, pH sensors, etc. This can render the sensors inaccurate, in an unpredictable way.

A growing trend in the fields of fermentation and cell culture is the use of multiple parallel small-scale vessels for optimizing process conditions, varying media constituents, selecting between different strains of organisms, and the like. Unfortunately, most existing devices for monitoring on-line cellular biomass are poorly suited to use in highly multiplexed parallel vessels. These poor suitability factors include the need for large volumes for accurate measurement, the requirement that the device be inserted through a port into the culture, and the inability to adapt the technology for multiplexing. These constraints make it cumbersome and cost-restrictive, if not impossible, to provide much-needed real-time monitoring of cell biomass for all vessels simultaneously in multiple parallel bioreactors.

Methods for monitoring biomass non-invasively, through the vessel wall, or through an optical window, have been developed in recent years. In U.S. Pat. No. 7,100,462 "Self Adjusting Sensor Mounting Device", methods and devices are described for reproducibly mounting a sensor to a wide variety of cylindrical and flat surfaces in a manner that automatically compensates for the curvature of the mounting surface.

In U.S. Pat. No. 8,603,772, "Particle sensor with wide linear range", methods and devices are described for measuring particulate concentration in vessels, where the response from multiple source-detector pairs is combined to provide a linear response over a wide range of particle concentrations. Also described, are methods and devices for confining the measurement to a specific volume within the medium, as methods and devices for performing rapid sequential measurement of particle concentration in multiple vessels.

In U.S. Pat. No. 8,405,033 "Optical sensor for rapid determination of particulate concentration" and U.S. Pat. No. 9,752,974 "Particle sensor with interferent discrimination", methods and devices are described for limiting the optical penetration depth of measurements of particle density by the use of light at wavelengths that are strongly absorbed by the medium, and matching the source-detector separation to the absorbance path length.

In view of the above, a need exists for devices that can read particulate concentrations accurately in multiple parallel small-scale vessels in the presence of bubbles as well as other nearby reflective objects, that is not prone to fouling, and that is linear over a wide range of biomass. Benefits could also be realized by adapting components mass-produced in other industries (e.g. telecommunications), for sensing applications. The present invention provides these and other features that will be apparent upon review of the following.

SUMMARY OF THE INVENTION

To provide flexibility in our particle detector systems, we determined it would be beneficial to provide, e.g., an array of optional light sources and/or light sensor types and/or locations on a detector contact head. Such a contact head can provide a selection of source/detector configurations (e.g., source/detector spacing, alternate fiber parameters) to optimally interact with any number of bioreactor walls and/or particle suspensions. Surprisingly, we found that certain available optic fiber connectors from the telecommunications industry can provide complementary features as an element of our non-invasive particle sensor concept. In a preferred embodiment, the multi-fiber connector can be a standard MPO (Multi-fiber Push On) connector, a part that is in common usage in the telecommunications industry for entirely different purposes. An adapter which includes a multi-fiber receptacle is used to hold the connector in a reproducible position against the wall of a vessel containing suspended particles (e.g. cell biomass in a liquid culture). At least two fibers are selected from among the available fibers in the connector; a first fiber comprising a light source conveyance means and a second fiber comprising a detected light conveyance means. Light conveyed by the source fiber is scattered by particles within the medium and a portion of the scattered light is collected by the detection fiber. The choice of source and detector fibers is selected according to the thickness of the vessel wall in order to minimize sensitivity to specular back-reflections from the vessel wall, while maximizing the range of sensitivity to changes in particle concentration.

In other embodiments non-MPO multi-fiber connectors are employed. In some such embodiments, multiple fibers are close-packed within an aperture of a fiber ferrule, and the separation between the source and detector fibers is determined by the choice of fiber types, and the relative position within the array. Adaptation of one such configuration for biomass measurement through an optical port in a single use fermentor is described.

Definitions

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" can include plural referents unless the content clearly dictates otherwise. Thus, for example, reference to "a component" can include a combination of two or more components; reference to "media" can include mixtures of media, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

As used herein, an "absorption coefficient" of a medium is the negative of the logarithm of the ratio of light transmitted through the medium to the light transmitted in the absence of the medium, divided by the path length travelled through the medium, as is understood in the art.

As used herein, an "detection cone" of a detector is the cone of detection rays surrounding the central optical axis of the detector at which the detected intensity is half that detected at the central optical axis.

As used herein, an "emission cone" of a light source is the cone of emission rays surrounding the central optical axis of the light source at which the light source intensity is half that at that the central optical axis.

As used herein, a "mean absorption path length" or "mean path length" in a medium is the inverse of the absorption coefficient of the medium.

A "sensor" of the methods and devices is a device component comprising at least one light source-detector pair in functional association.

As used herein, "substantially" refers to largely or predominantly, but not necessarily entirely, that which is specified.

The term "about", as used herein, indicates the value of a given quantity can include quantities ranging within 25% of the stated value, or optionally within 10% of the value, or in some embodiments within 1% of the value.

BRIEF DESCRIPTION OF THE DRAWINGS

FIGS. 6 A-C depict three different perspective views of an example adapter of the present invention for attaching a multi-fiber connector to a vessel, which comprises a receptacle for a for a multi-fiber connector that is integral to a vessel adapter for holding the connector against a vessel.

LIST OF COMPONENTS DEPICTED IN FIGURES

Figure 1A:
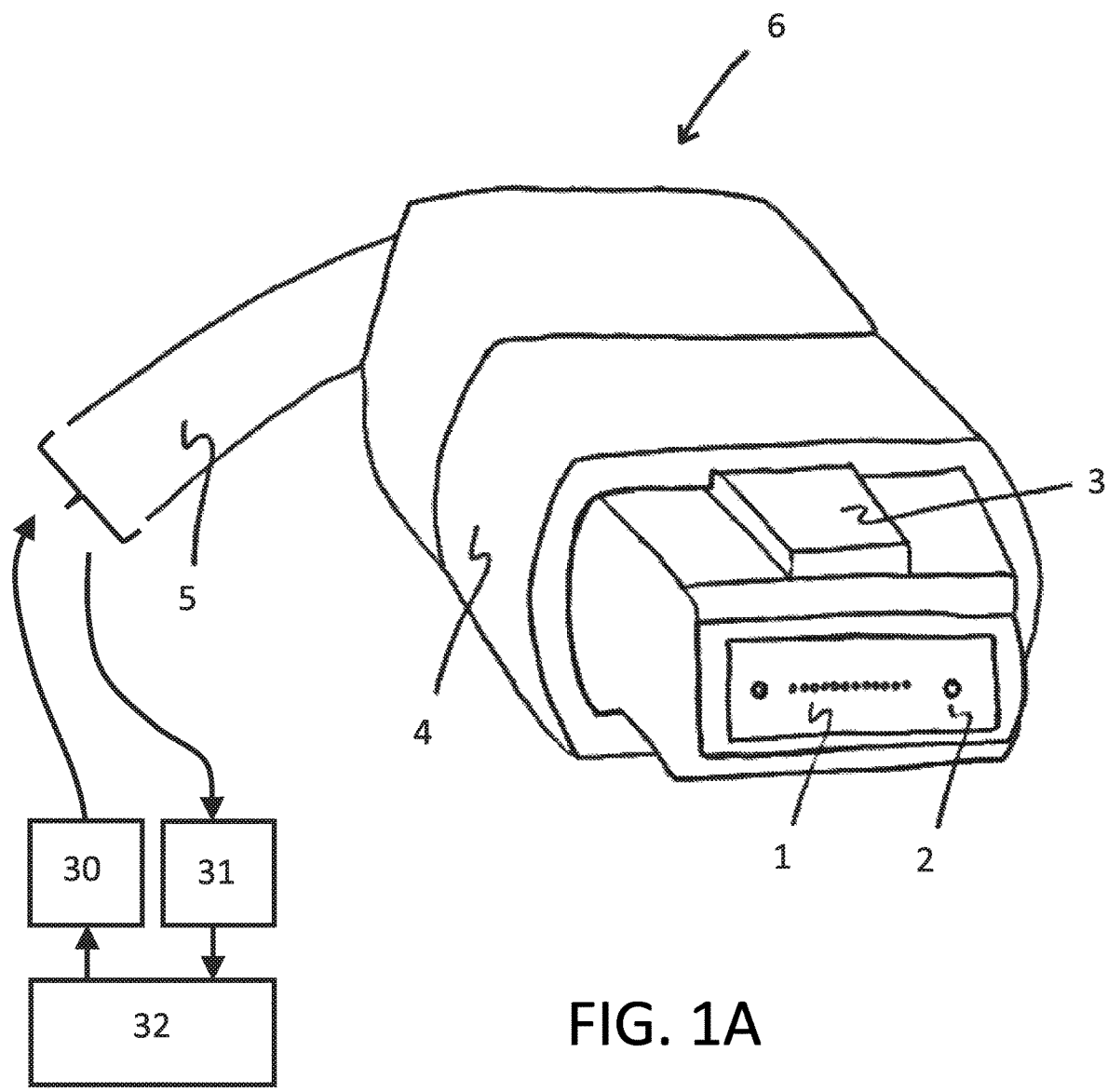
FIG. 1A depicts a multi-fiber connector with attached cable, connected to a light source, detector, and processor.

1—optical fibers in a multi-fiber connector
2—positioning aperture in a multi-fiber connector
3—key in a multi-fiber connector
4—spring-loaded latch in a multi-fiber connector
5—cable attached to a multi-fiber connector
6—multi-fiber connector with attached cable
7—vessel adapter for attaching a multi-fiber connector to a vessel
8—vessel
9—face of vessel adapter that is attached to a vessel
10—cavity in vessel adapter for accommodating a multi-fiber receptacle
11—flexible hinge on vessel adapter
12—receptacle for multi-fiber connector
14—reflectance standard
15—cavity for holding reflectance material
16—vessel adapter hooks
17—retaining clip
18—channel
19—flexible tab
21—retaining ring
22—spring
23—spring cavity
24—cable cavity
25—latch
26—optical window
27—optical port
28—port ring
29—outer ferrule ring
30—light source
31—detector
32—processor

DETAILED DESCRIPTION

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments as suggested in the present description, and may be satisfactorily applied for the measurement of any material which may exhibit similar behavior that are also intended to be encompassed within the spirit and scope of the invention.

The detailed description set forth herein will make reference to the measurement of biomass in a liquid culture. The term "biomass" as used in this patent application, refers to the concentration of biological material, such as cells or microorganisms, e.g., suspended in a media. What is meant here and elsewhere in the patent application by "concentration" is the number of a type of particle, weight of a type of material, or volume of a type of material found in a given volume or weight of a medium.

Optical Density (OD) is defined as:

$$OD = -F\log_{10}\left(\frac{I}{I_0}\right)$$

where light intensities are measured after transmission through a medium containing suspended particulate matter (I) and through the same medium in the absence of particulate matter ($I_0$). It is common in the biofermentation field to measure and refer to biomass according to the optical density measured at a particular wavelength, such as 600 nm ("OD600"), through a 1 cm path length cuvette, with a commercial spectrophotometer. When measuring OD using a spectrophotometer it is necessary to dilute the sample to have an OD in a linear range of response (commonly OD<1, but more ideally OD between 0.05 and 0.2) and then scale the measured OD by the dilution factor, F. This type of measurement is herein referred to as "Offline OD" measurement, to distinguish it from the real-time ("Online") measurement allowed by the methods and devices for the present invention. For mono-disperse cells a linear relationship between biomass and OD generally holds.

The method(s) and instrument(s) of the present invention may also find application in liquid suspensions of solids other than biomass as well as in solutions. For example, the particulate content in milk, the rate of polymerization in a chemical system or the turbidity of water may be measured by application of the method(s) and/or instrument(s) of the present invention. Similarly, the present invention may be utilized to determine the amount of gas in a liquid phase, such as the concentration of gas bubbles in a liquid medium. In addition, the attenuation of radiation by absorption may be used to measure the concentration of components dissolved in solution, by application of the present invention.

The method and instruments of the present invention may also be useable in the gas phase. For example, in industrial plants using smokestacks, the amount or concentration of a specific component of the effluent gas may be measured by application of the present invention. As another example, the present invention may be used to measure the particulate content of a gas for the purpose of smoke or fire detection. As yet another example, the present invention may be used to measure the concentration of a particular component of a gas, such as the concentration of carbon dioxide in a mixture of gases or the density of fog or smoke in the flight path of an airplane.

In addition, the method(s) and/or instrument(s) of the present invention may be utilized to monitor materials in the solid state and to monitor transformation of materials between states. For example, the present invention may be used to monitor the conversion of a liquid to the solid state, such as gel formation, or crystallization. Thus, although the hereinafter-set-forth descriptions often refer specifically to the measurement of the biomass in a liquid culture, it will be appreciated that the method(s) and instrument(s) of the present invention are also applicable in other liquids and in gas and solid media applications.

Description of Exemplary Devices and Methods

Figure 2:
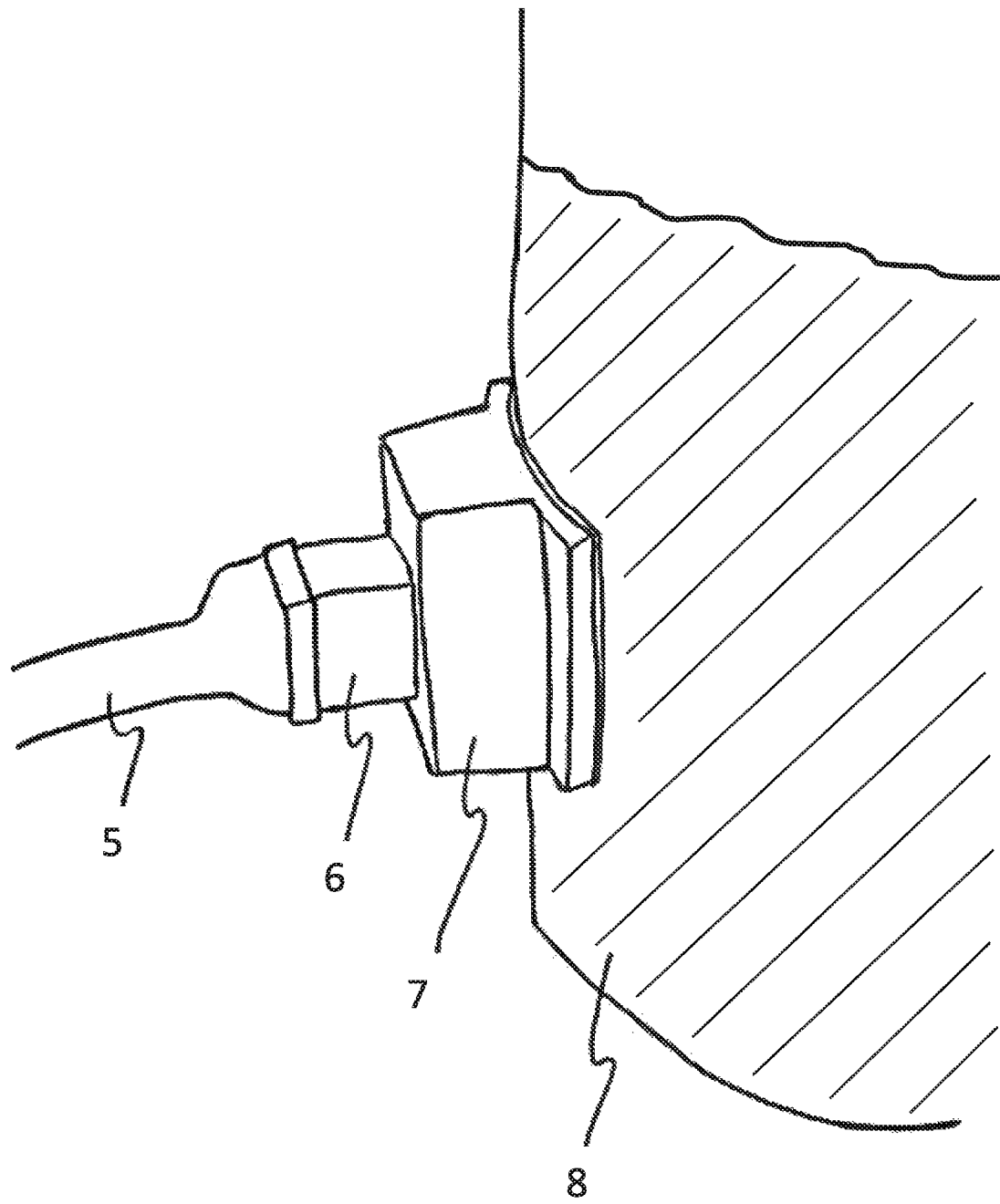
FIG. 2 depicts a multi-fiber connector attached to a vessel using an adapter, thereby functioning as a particle sensor for the media contents within the vessel, according to the teachings of the present invention.

FIG. 2 depicts an embodiment of the invention in which a multi-fiber connector 6, is connected to a vessel adapter 7. The vessel adapter comprises a receptacle which holds the multi-fiber connector securely against a vessel 8, containing a medium in which particles are suspended. A cable 5, housing optical fibers is connected to a base unit. The base unit contains a light source and a detector (collectively referred to herein as opto-electronic components) which are coupled to the fibers in the cable. The fiber connected to the light source (hereafter referred to as the "source fiber") conveys light into the media in the vessel, where it is scattered by the suspended particles. The fiber connected to the detector (hereafter referred to as the "detector fiber") captures a portion of the scattered source light and conveys it to the detector where it is amplified and converted into a signal. The base unit also contains a micro-processor which converts the detected signal into particle concentration and makes it available for reporting.

Multi-Fiber Connectors and Receptacles

The present invention uses, e.g., multi-fiber connectors and receptacles, in common usage in the telecommunications industry, and adapts them for usage as particle sensors. One such multi-fiber connector, known as Multi-fiber Push On (MPO) connectors in the telecommunications industry, is depicted in FIG. 1A. This class of connectors will be collectively referred to hereafter as MPO connectors. The term multi-fiber connectors is used herein to more generally describe MPO connectors as well as other connectors that allow multiple fibers to be coupled with a single connection.

The MPO connector depicted in FIG. 1A contains several features that make it well-suited not just to its originally intended function of reproducibly connecting fibers to other fibers or to opto-electronic components, but also to use as a particle sensor according to the present invention. Two positioning apertures 2 located on the face of the connector adjacent to the optical fiber 1 faces, provide a means of orienting the fiber face with high reproducibility, when matched with mating male features in a mating connector or receptacle. The key 3 in the connector ensures that the orientation is always consistent when mated into a receptacle. The spring-loaded latch 4, provides a means of urging the face of the connector against a mating surface. Optic fibers in the fiber optic cable 5 function to transmit interrogating light from one or more light sources 30 to a media of interest in a vessel and return light scattered back by particles to one or more detectors 31, which generates an analog or digital signal that is received and interpreted by a processor 32.

The vessel adapter 7, depicted in FIG. 2, incorporates an MPO receptacle into its design. When the MPO connector is plugged into the receptacle, the spring-loaded latch 4 is engaged into the receptacle and the optical fibers are forced into intimate contact with the face of the vessel.

Figure 1B:
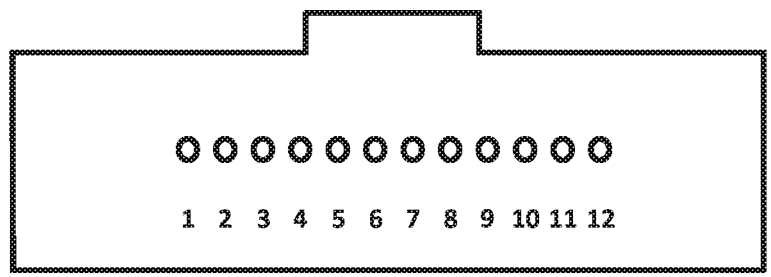
FIG. 1B depicts the front face of a multi-fiber connector with 12 optical fibers equally spaced along a single line.

MPO connectors typically comprise one or more rows of optical fibers 1 within the same connector. The number of fibers within a row is commonly 12 or 16. The number of rows is commonly 1, but can include 2 or more rows. For the present invention a preferred embodiment is a single row of 12 fibers, spaced 250 µm apart (center-to-center), as depicted in FIG. 1B (in which the individual fibers have been numbered). The vessel adapter is designed so that the row of fibers is oriented parallel to the flat dimension of the vessel to which it is attached. In this manner all fibers are forced into functional contact with the vessel wall, regardless of the radius of curvature of the vessel. As a result, the particle reflectance is reproducibly measured across vessels having different shapes, but the same wall thickness.

MPO connectors are most commonly designed to accommodate fibers with clad diameter of 125 µm. Both single mode and multi-mode fibers are commonly available with this clad diameter. In a preferred embodiment of the present invention a single mode fiber is used for the light source fiber, while a multi-mode fiber is used for the detection fiber. Advantages of using a single-mode over multi-mode fiber for transmitting the source light are that single-mode fibers are typically lower in cost and have reduced sensitivity to bending of the fiber. A commonly used single mode fiber, appropriate for the present invention, is SMF28e, manufactured by Corning.

The optical fiber used to convey the detected light of the present invention generally needs to be multi-mode in order to have a sufficient collection area for diffuse light scattered by the particles being measured. For this reason, multi-mode fibers with as large a core diameter as possible may be desirable. In a preferred embodiment, a multi-mode fiber with 105/125 µm core/cladding is used for conveying the detected light. In other embodiments, multi-mode optical fiber is used to convey both the source and detected light.

In other embodiments, the multi-fiber connector is other than an MPO-type connector. In some such embodiments, a connector ferrule containing a single aperture is used to accommodate multiple fibers in a close-packed arrangement, one specific embodiment of which is described in Example 3 and depicted in FIG. 12A. The advantage of this single aperture design is that precise source-detector separations may be achieved by appropriate selection of one or more fiber types. In Example 3, two fiber types are selected, the larger of which is used solely as a structural element, in order to maintain a fixed and reproducible separation between the smaller fibers, two of which are selected as the source and detector fibers. In other embodiments, different pairs of fibers are selected according to the desired source-detector separation to be achieved (e.g. as appropriate for measurement through a particular vessel wall thickness). In other embodiments, a separate disk is constructed, such as by molding glass, containing apertures for the source and detector fibers. The disk is then affixed to the front of the multi-fiber connector.

The multi-fiber connector described in Example 3 was fabricated using both a customized ferrule and adapter. However, in other embodiments the multi-fiber connector and/or adapter make use of one or more off-the-shelf parts (such as from the telecom industry), and adapt them for the specific purpose of non-invasive particle measurement. In some such embodiments, a standard LC, FC, SM, SC, ST, or similar fiber optic connector type, originally designed to accommodate only a single fiber optic connection, is adapted to accommodate multiple fibers, such as by use of a ferrule with a relatively large aperture, and inserting multiple fibers into the aperture in a close-packed arrangement. In further embodiments, the receptacle portion of a standard single fiber connector is incorporated into a vessel adapter of the present invention, providing a secure and reproducible of attaching the fiber connector to the surface of a vessel, for the purpose non-invasively measuring particle concentration. In other embodiments, the ferrule includes two or more apertures, allowing multiple fibers to be directly inserted into the ferrule and held at fixed positions.

Selection of the Source and Detector Fibers

The selection of which fibers within the available array of fibers of a multi-fiber connector to use for the purpose of creating a particle sensor of the present invention is next considered. Two primary considerations in this regard are: (1) interference from specular reflections for the wall of the vessel, and (2) maximizing the range of sensitivity to changes in particle concentration. At short separation distances, the cone of light emitted by the source fiber may overlap with the cone of light collection for the detection fiber within the wall of the vessel. In this case, the detection fiber may collect light scattered by the wall of the vessel, particularly at the interface between the vessel and the medium containing the scattering particles. Reflections from a macroscopic surface, such as the wall of a vessel, is referred to herein as a specular reflection. Especially when the concentration of scattering particles in the medium is low, specular reflections have the potential to overwhelm the detected diffusely reflected light contributed by the particles of interest. This effect can be seen in FIG. 9C, described in Example 1, in which the MTP #3 detection fiber (represented by open circle markers in the Figure), separated from the source fiber by only 500 µm, is sensitive to the specular reflections from the 2 mm thick vessel wall. The measured reflectance for this detection fiber is nearly flat until the yeast concentration is well above 1 g/L. In contrast, by selecting a detection fiber (MTP #4, represented by "x" markers in FIG. 9C) that is separated from the source fiber by 750 µm, the influence of specular light on the measured signal is greatly diminished, and changes in the yeast concentration less than 0.1 g/L are readily resolved.

To further reduce the effects of specular reflectance, greater source-detector separations may be selected. However, with the increase in source-detector separation also comes a decrease in the signal size of the diffuse scattering from the particles of interest. Further, at high particle concentrations a roll-off of the reflectance signal is seen with increasing severity as the source-detector separation is increased (again referring to FIG. 9C; see for example the MTP #8 response, represented by diamond-shaped markers). For this reason, the optimal source-detector separation may vary with the thickness of the vessel wall.

Theoretical modeling, as described in U.S. Pat. No. 9,752,974 (FIG. 8, Table 6, and Example 6), which is incorporated here in its entirety by reference, was used to predict the optimal source-detector separation and the corresponding optimal fiber number in an MPO fiber connector, as summarized in Table 1. For the purposes of the calculations, the source fiber core diameter was 9 µm, the detector fiber core diameter was 105 µm, the numerical aperture of both fibers was 0.22, and the indices of refraction of the vessel wall and medium were 1.5 and 1.33, respectively. The fiber-to-fiber separation in the MPO connector was 250 µm, and the source fiber was assumed to be connected to fiber number 1.

TABLE 1

Predicted optimal source-detector fiber separation for different vessel wall thicknesses.

| Vessel Wall Thickness (mm) | Optimal Source-Detector Separation (mm) | Optimal Detection Fiber Number in an MPO Connector |
|---|---|---|
| 1 | 0.54 | 3 |
| 2 | 0.83 | 4 |
| 3 | 1.1 | 5 |
| 4 | 1.4 | 7 |
| 5 | 1.7 | 8 |
| 6 | 2.0 | 9 |
| 7 | 2.3 | 10 |
| 8 | 2.6 | 11 |
| 9 | 2.9 | 12 |

Table 1 predicts that vessel walls having thicknesses up to 9 mm could be accommodated by a standard 12-fiber MPO connector, with 250 µm spacing between fibers. In a preferred embodiment of the invention, one source and one detector fiber out of the array of 12 MPO fibers are employed in the particle scattering measurement. This embodiment has the advantage of only requiring 2 connectors, such as a duplex LC connector at the opposite end of the cable. Under this arrangement, different sensors would need to be used for different wall thicknesses.

In an alternate embodiment, more than one light source or detector fiber is connected to the multi-fiber connector. With this arrangement, it would be possible to use the same sensor on vessels with different wall thicknesses. The user could select the appropriate fibers to use for a given vessel, such as by connecting only the appropriate connector into a receptacle on a base unit which houses the opto-electronic components. Alternately, a fiber switcher is employed which automatically selects the correct fiber. In one embodiment this is performed under software control, whereby the user selects the vessel type, and then the software instructs the switcher to select the appropriate fiber. In yet another alternative arrangement, instead of using a switcher, multiple fibers are connected to multiple optoelectronic components (light sources and/or detectors).

In some circumstances it may be desirable that the appropriate source-detector spacing is automatically selected, without any need for user invention. In one embodiment, this is accomplished by placing the sensor on the vessel to be used, when it is only filled with media (e.g. prior to inoculation with cells). The signals across multiple source-detectors is compared, and the closest source-detector pair having a signal below a pre-set threshold is selected.

Figure 12A:
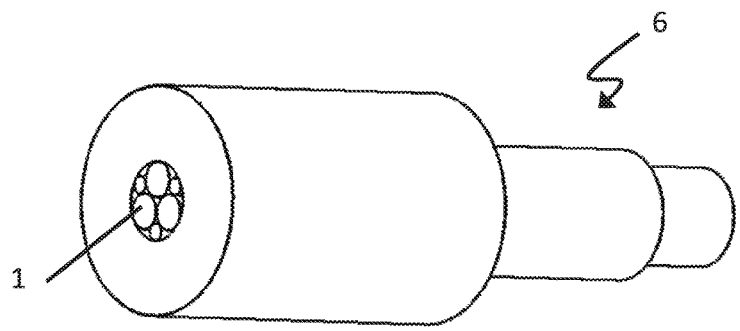
FIGS. 12A-C depict a vessel adapter of the present invention designed to accommodate a multi-fiber connector into an optical port of a single use fermentor to enable measurement of biomass according to methods of the present invention, as further described in Example 3.

In other embodiments the source and detector separation is determined by selecting from among a close-packed arrangement of fibers, such as depicted in FIG. 12A.

Vessel Adapter

Example vessel adapter designs are depicted in FIGS. 3A-E and 12. In the design depicted in FIG. 3A, the face of the vessel adapter 9, includes two flat surfaces angled towards each other, forming a V-shape that can accommodate a variety of different vessel diameters. The cavity 10 in the vessel adapter is designed to accommodate a standard MPO fiber optic receptacle. When an MPO connector is plugged into the receptacle, the face of the connector is pushed against the wall of the vessel by the spring mechanism in the connector.

Figure 3A:
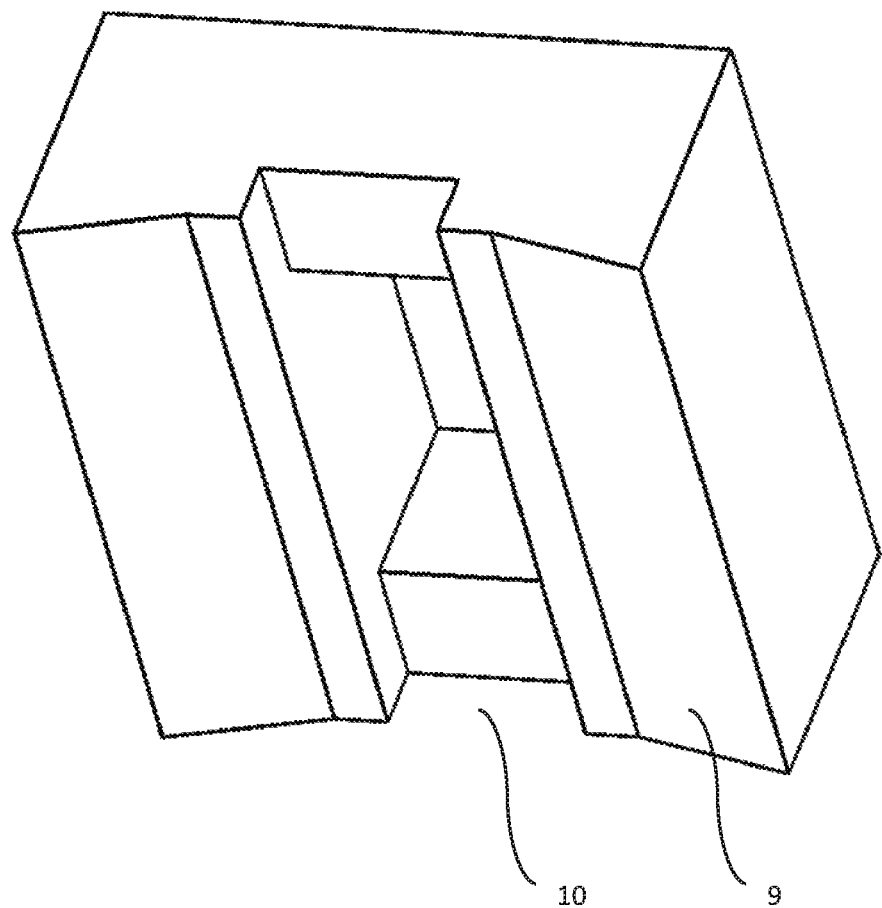
FIGS. 3 A-E depict various examples of adapters for attaching a multi-fiber connector to a vessel, according to the teachings of the present invention.
Figure 3B:
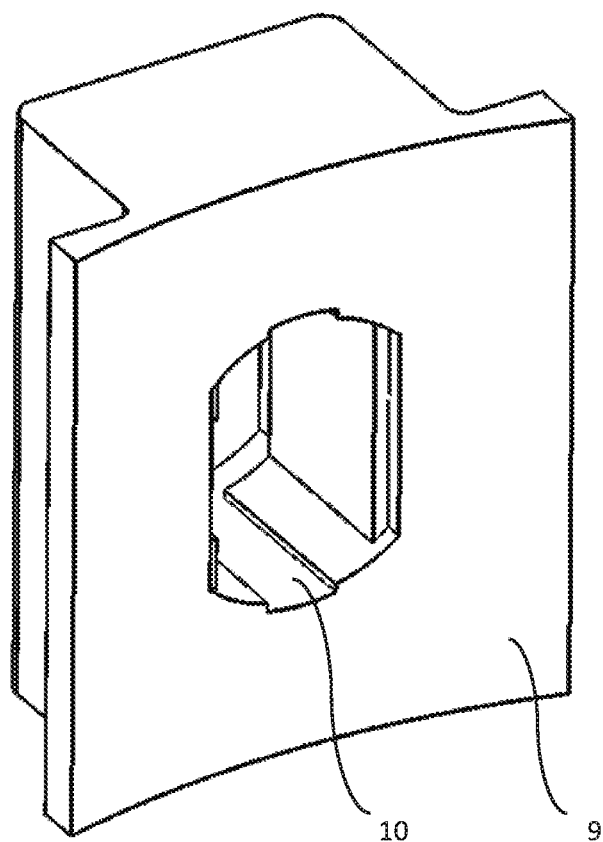

In the design depicted in FIG. 3B, the face of the vessel adapter 9 is extended beyond the bounds of the receptacle-containing portion, and is shaped to match the surface of the vessel to which it is to be attached, thereby providing a larger surface area for stabilization and attachment of the adapter to the vessel surface. The cavity 10 contains features that replicate the design of the exterior portion of an MPO receptacle. The interior portion of an MPO receptacle, which contains smaller, more high-precision features would be added separately (e.g. glued into place) during manufacture. This design potentially lowers the product cost by using an off-the-shelf mass-produced part for the complex interior of the receptacle.

Figure 3C:
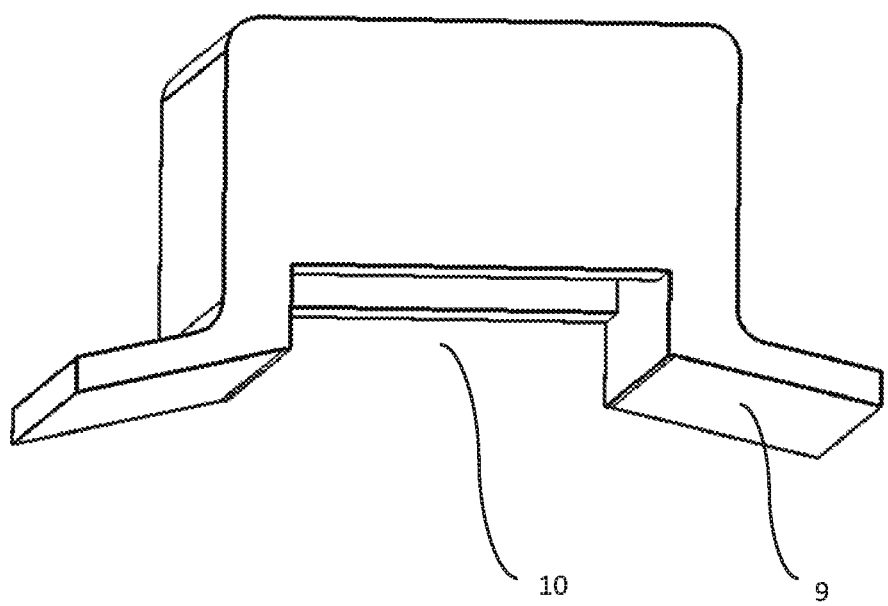
Figure 3D:
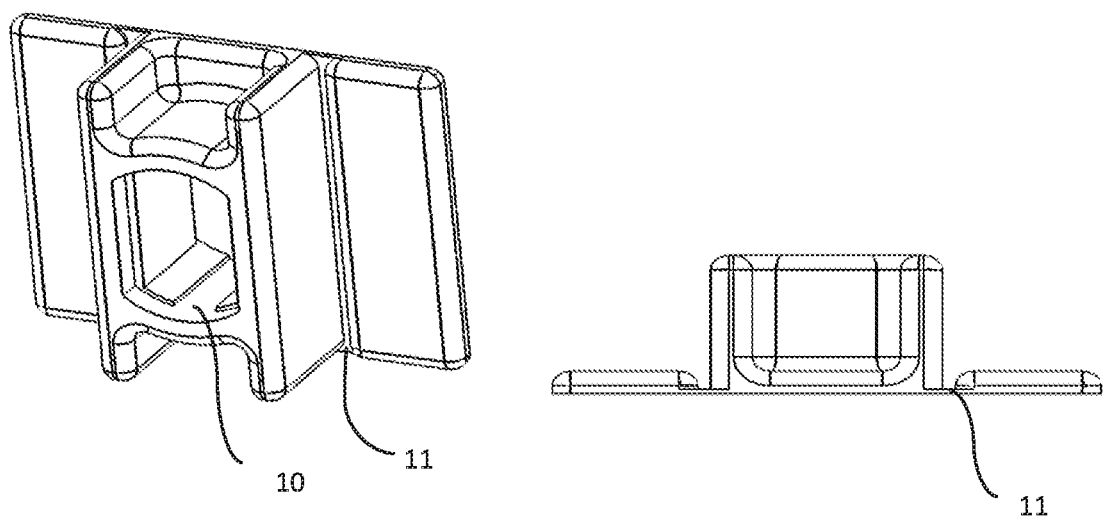
Figure 3E:
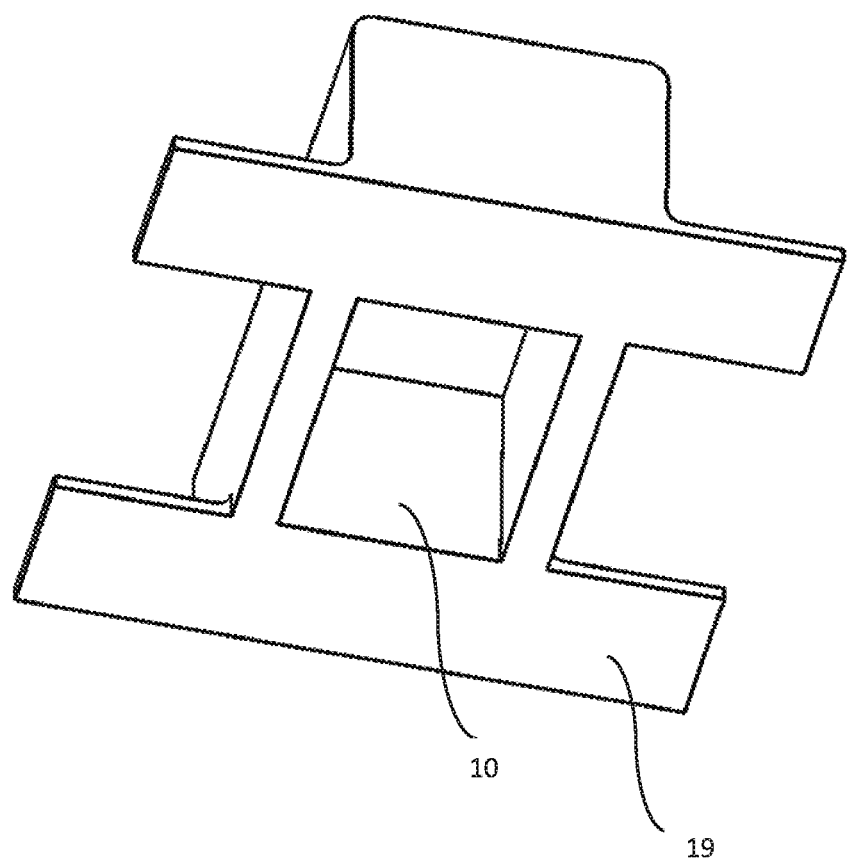

The design depicted in FIG. 3C combines the V-shaped element of the 3A design with the extended surface area of the 3B design. A flexible hinge 11 is provided in the design depicted in FIG. 3D. The flexible hinge allows the adapter to accommodate a very wide range of vessel diameters while maintaining a high surface area for contact between the adapter and the vessel. The design depicted in FIG. 3E includes four separate and flexible tabs 19 on the face of the vessel adapter. This design may be particularly suitable for attachment to cone-shaped flasks, such as shake flasks or Erlenmeyer flasks.

FIG. 4 depicts three perspective views of a vessel adapter constructed based on the design depicted in FIG. 3B. The outer portion of the vessel adapter was 3D printed from acrylonitrile butadiene styrene (ABS). The design is also well suited to fabrication as a molded part. The black inner portion is the interior of an off-the-shelf MPO receptacle 12. Depictions of the same vessel adapter after plugging an MPO connector into the receptacle are shown in FIG. 5. When connected but not attached to a vessel, the optical face of the MPO connector protrudes slightly beyond the face 9 of the vessel adapter, ensuring that the fibers 1 will be in contact with the face of the vessel when the adapter is attached to a vessel. The spring mechanism built into the MPO connector provides a resistive force which urges the fibers against the vessel, and maintains firm contact across small changes in the positioning of the MPO connector within the vessel adapter.

In another embodiment the MPO receptacle is designed into the vessel adapter so that their separate assembly is not required. An example embodiment is depicted in FIGS. 6A to 6C, from three different perspectives. A keyed channel 18 traverses the vessel adapter providing a shape that mates with the key 3 in a standard MPO connector, thereby ensuring that when attached to a vessel 8, the line of optical fibers 1, is held perpendicularly to the surface along the flat axis of the vessel. When the MPO connector is plugged into the vessel adapter, retaining clips 17 secure the connector inside the vessel adapter unless the latch 4 within the MPO connector is pulled. A flexible hinge 11 in the vessel adapter allows the adapter to conform to the surface of vessels having a wide range of diameters. In some embodiments, such as depicted in FIG. 6B, the surface 9 of the vessel adapter includes a slight radius of curvature to lessen the range of hinge motion needed to accommodate a range of vessels sizes. By incorporating the MPO receptacle directly into the design of the vessel adapter, the cost and reproducibility of manufacturing may be reduced, by allowing the part to be created, for example, as a single printed or molded part.

In some embodiments the vessel adapter is designed for a single use, whereas the sensor is reusable. For example, when used on single use fermenters or bioreactors the vessel adapter may be disposed of along with the vessel, so that detachment and re-attachment of the vessel adapter across multiple vessels is not required.

In other embodiments the vessel adapter is designed to allow for secure and reproducible insertion of a multi-fiber connector into an optical port in a vessel, such as depicted in FIG. 12 and Example 3. In such embodiments, where the measurement window is flat, a non-linear arrangement of fibers may provide advantages, such as allowing for a more compact design, and improving the ease of manufacturing.

Attachment of the Adapter to the Vessel

In many applications where continuous monitoring of particle concentration is desired, a method of affixing the adapter to the vessel is needed. In a preferred embodiment, a double-sided adhesive is used in an intermediate layer between the adapter and vessel. This method of attachment has the advantage of convenience. In applications where there is limited available surface area on the vessel, such as bioreactors surrounded by a heating element, the small footprint afforded by adhesive attachment is another important advantage. Typically such heating elements will include a small opening for vessel viewing, on the order 1"×1" or more. In some embodiments, the height and width of vessel adapter and underlying adhesive are designed to be equal to or less than the height and width of a vessel viewing port. In other embodiments the width of the vessel adapter may be slightly greater than that of the viewing port, and a low profile portion of the vessel adapter is slipped between the heating element and the vessel, potentially making the attachment between the adapter and vessel more secure. For use with re-usable (e.g. glass) vessels, an adhesive may be selected that is removable without leaving a residue. In some embodiments the adhesive is activated by the application of pressure. In other embodiments, a primer is used on the surface of either the vessel adapter, the vessel itself, or both, in order to improve the adhesion of the tape to the primed surface. A suitable primer in many embodiments is 3M part number 94. In yet further embodiments, the adhesive is resistant to moisture, and forms a moisture barrier between the sensor and vessel. Such embodiments have the advantage of preventing moisture from potentially interfering with the scattering measurement. The adhesive may form a continuous seal around the perimeter of the multi-fiber connectors. In other embodiments, the seal is formed on at least 3 sides, so that liquid overflow from the vessel is prevented from entering the space between the multi-fiber connector and the vessel. For some applications, such as for use with a vessel adapter that is intended for single use, it will be desirable that the adhesive can only be used once, and either tears or substantially loses its adhesive strength when removed. A double-sided adhesive suitable for many embodiments of the invention is 3M part number 5925.

Particularly for applications in which it is desirable for the vessel adapter to be reused or repositioned frequently, a strap attached to the adapter that surrounds the vessel may be used to secure the vessel adapter. The strap may be elastic, having the advantage of conforming to a range of vessel diameters, without need for adjustment. Alternately, the strap may be constructed from a fabric and securing to the vessel is accomplished by cinching the strap through a buckle. In some embodiments, a latch is also employed as a mechanism of tightening the strap.

In yet other embodiments the means of attachment of the vessel adapter is tailored to the specific geometry of the vessel. The vessel adapter depicted in FIG. 12 and further described in Example 3 is attached through a port on a single use fermentor that comprises a ring 28. The ring serves as a convenient attachment point for a latch 25 on the vessel adapter, which engages with the ring under spring force.

Light Source Selection

The parallel arrangement of the fibers in a multi-fiber connector (e.g. MPO connector), and the limited cones of emission and detection inherent to optical fibers, in tandem provide the advantage of reduced sensitivity of the optical collection efficiency to the distance between the sensor and the medium being measured. The result is that changes in vessel diameter and minor variations (e.g. <1 mm) in the wall thickness of the vessel may cause little or negligible variation in the measured reflectance. In some embodiments, the numerical aperture and diameter of the fibers used in the multi-fiber connector are adjusted in order to further reduce sensitivity to variations in wall thickness. For example, by the selection of optical fibers with lower numerical aperture (e.g. 0.11 instead of 0.22), and/or with reduced core diameter (e.g. 50 or 62.5 µm core instead of 105 µm), the sensitivity of the measurement to wall thickness may be reduced. This reduction in wall thickness sensitivity will typically need to be balanced with the attendant loss in signal magnitude, since, particularly for the detection fiber, reductions in core diameter or numerical aperture will result in proportional reduction in the collection efficiency for diffusely scattered light.

Another point of necessary consideration when employing optical designs with parallel source and detector central optical axes measuring back-reflectance, is sensitivity to objects other than the particles of interest. At low particulate concentrations, if light at the source wavelength travels unimpeded through the medium, reflections from other objects in the vessel have the potential to interfere with the measurement. In particular, when measuring low biological cell concentrations (e.g. <1 g/L dry cell weight) in aqueous media in a vessel such as a bioreactor, if the source wavelength is only weakly absorbed by the medium, specular scattering from reflective (e.g. metallic) objects such as bioreactor impellers and probes, or the wall of the vessel itself can easily overwhelm the signal due to diffuse reflections from the biological cells. This is particularly true for small fermenters or bioreactors (such as <1 L capacity), where the unimpeded volumes available for optical measurements are necessarily limited. The small size, potentially low cost, and readily multiplexed nature of the present invention is particularly well-suited for use in multiple parallel miniature bioreactors, such as are commonly used for optimizing across process conditions, media composition, multiple bacterial strains, etc. A key feature of the invention embodiments applicable to these conditions is selection of a light source at a wavelength at which the light is significantly attenuated by absorption within the medium.

Figure 11:
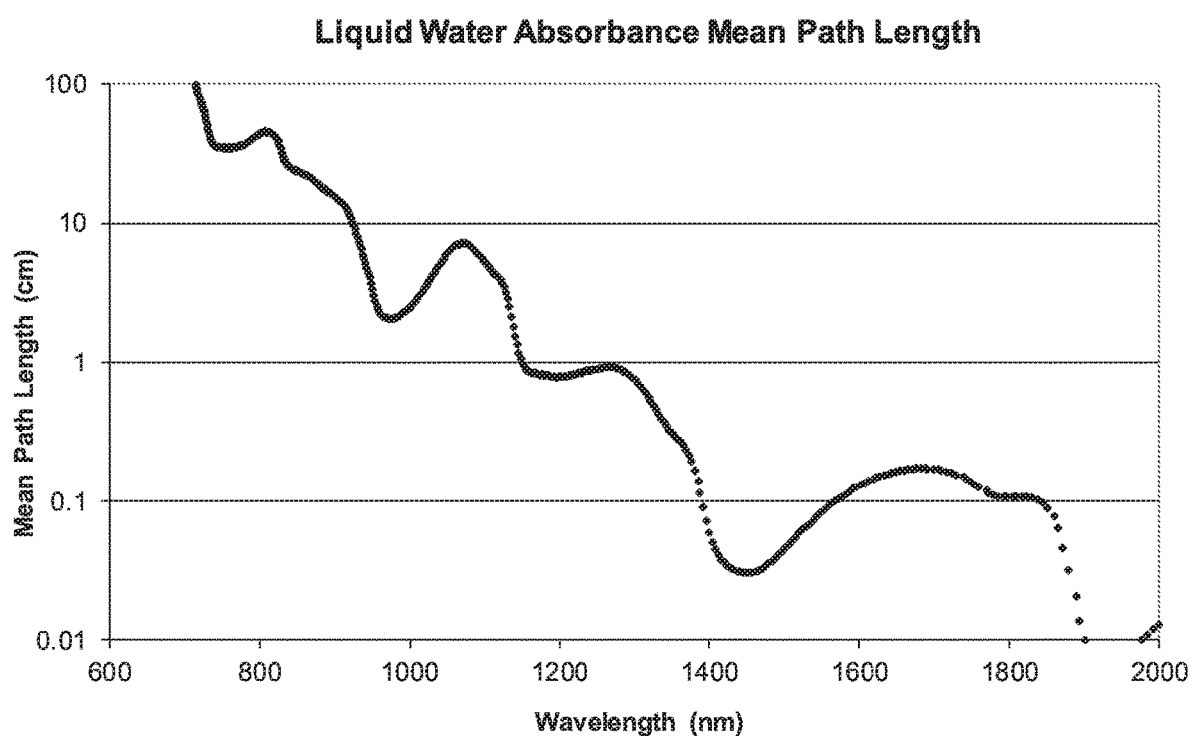
FIG. 11 is a graph showing the mean path length of light through liquid water as a function of wavelength.

For aqueous media, selection of source wavelengths in the wavelength range of about 1100 to 1400 nm may provide the appropriate balance between low sensitivity to non-biological objects in the vessel, while maintaining sufficient sensitivity to the particles in the media. Referring to FIG. 11, in the absence of scattering particles, the mean pathlength of light through liquid water is greater than 10 cm for wavelengths below 900 nm, extending through the visible region of the spectrum. In this region of the spectrum, light will therefore be able to travel relatively unimpeded through a vessel filled with water, and it will be difficult to avoid the interference from non-biological objects. On the long wavelength side, for example at wavelengths of 1400 nm and longer, the mean pathlength is less than 2 mm. At such long wavelengths, the penetration of light into the aqueous medium will be so shallow as to limit the sensitivity of a measurement of particle scattering measurements.

The region between about 900 and 1400 nm provides a spectral window where the path length is short enough to limit unwanted interference from specular reflections, while maintaining sufficient sensitivity to scattering from particles. More specifically, the spectral region between about 1100 nm and 1400 nm, and particularly wavelengths between about 1300 and 1350 nm, are particularly well-suited to the purposes of the present invention. The ready available of light sources in the 1300 to 1350 nm for telecommunications purposes, makes this choice of wavelength particularly suitable. 1310 nm is one of the most commonly used source wavelengths in the telecommunications industry due to its suitability for fiber transmission over long distances (e.g. kilometers) with low attenuation loss. It is also well suited to the purposes of the present invention—the mean pathlength in water at 1310 nm is about 6 mm, and after traveling through about 3 cm of water the light will be almost entirely extinguished. Objects that are further than 3 cm from the sensor will therefore have no effect of the measured reflectance. In other embodiments of the invention, suitable for vessels in which the available space for measurements is even further limited, a source wavelength of about 1330 nm is selected. At this wavelength objects located further than about 2 cm from the sensor will not contribute to the measured reflectance.

Calibration and Verification

Figure 7A:
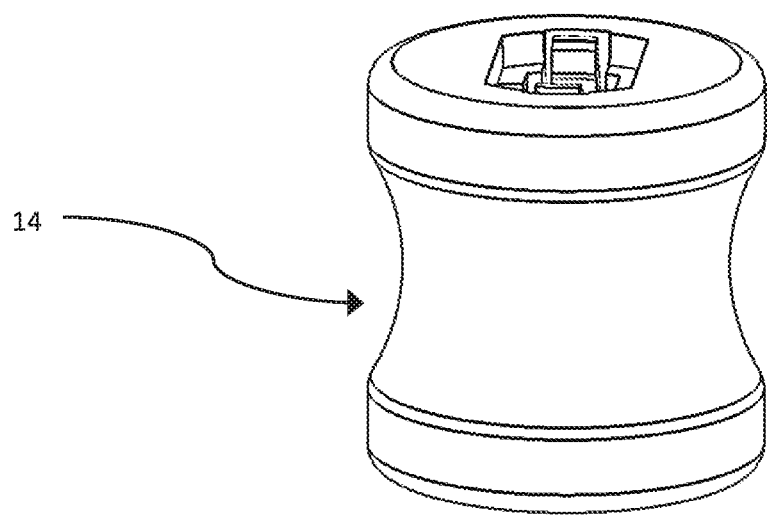
FIGS. 7 A-C depict three different perspective views of a reflectance standard of the present invention into which a multi-fiber connector can be quickly and reproducibly attached by means of an adapter, thereby providing a means of easily calibrating or verifying sensor performance.
Figure 7B:
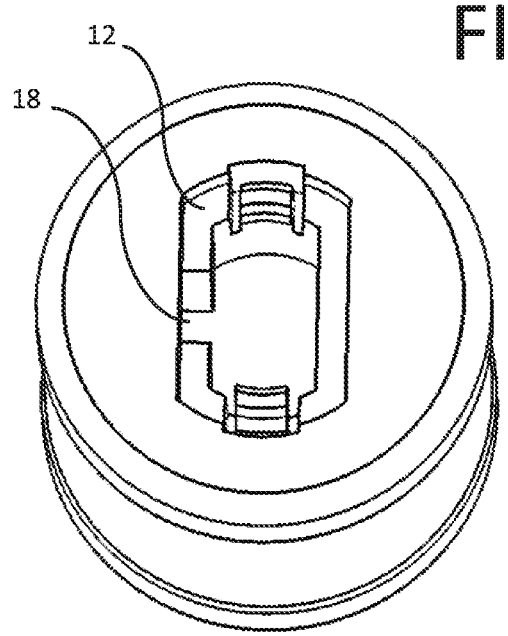
Figure 7C:
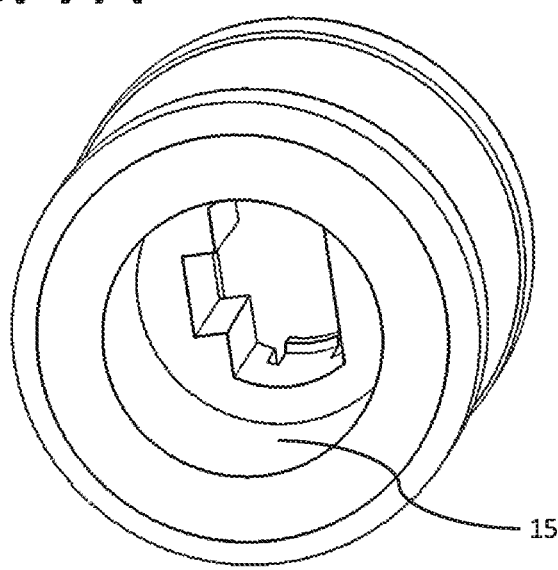

An advantage of the use of mass-produced multi-fiber connectors in many embodiments of the present invention is that they may have higher part-to-part replicability than parts which are individually made or manufactured on a small scale. Nevertheless, a means for compensating for device-to-device variations is provided. These means include the use of one or more reflectance standards, an example of which is depicted in FIG. 7. The standards comprise several features including: (1) a reflective material that is stable over time, (2) a means of reproducibly attaching the multi-fiber connector to the standard, and (3) a means of shielding the reflectance standard from outside interference, such as ambient light or other reflective objects in the vicinity of the standard.

In one embodiment, the reflective material is a solid plastic. Examples of suitable materials for providing a stable high reflective signal are Teflon, Kynar, epoxy impregnated with scattering particles, or other plastics or resins which substantially scatter light. In the example depicted in FIGS. 7A-C, a Teflon dowel may be embedded in a cavity 15 within the standard and used to provide a reproducible high reflectance signal. Examples of suitable materials providing a stable low reflectance signal are black plastics with a dull surface finish. In the example depicted in FIG. 7, black ABS may be embedded in the standard, and used to provide a reproducible low reflectance signal. A cap may be used to hold the standard material in place. In other embodiments, the material from which the standard is constructed is used as the reflectance material, precluding the need to include a separate cavity and cap.

In practice it has been found that many plastic materials, such as Telfon, that appear visibly uniform to the naked eye, actually have substantially variable reflectance as measurements are made across their surface. For this reason, to improve the reliability of the reflectance standard measurement, in many embodiments it is desirable to include a means of reliably attaching the sensor to the reflectance material in the same position and orientation across repeated measurements. This is accomplished, in the example depicted in FIG. 7, through the incorporation of a multi-fiber receptacle (which is in this case an MPO receptacle), that allows the multi-fiber connector to be plugged into the standard. In many embodiments the reflecting material is situated just below the receptacle, so that when the connection is made, the face of the multi-fiber connector makes contact with the surface of the reflecting material, and is urged against it under the spring force provided by the latch in the multi-fiber connector. The key 3 (see FIG. 2) provided in multi-fiber connectors and the matching channel 18 (see FIG. 7) built into the receptacle provide a reliable method of ensuring that the same orientation of the sensor is maintained relative to the reflective standard, each time it is plugged in.

In some embodiments, the use of only a single high-reflectance standard will be sufficient to standardize and account for the variation across different manufactured sensors of the present invention. In such embodiments, a simple multiplication factor based on a comparison of the reflectance on different sensors, may be sufficient to account for variation. In other embodiments, particularly where the cleanliness of the fibers or the quality of the optical finish on their end faces is of potential concern, the additional use of a low-reflectance standard may provide benefit. The low standard measurement may show improved sensitivity to optical imperfections on the fiber faces, providing a mechanism by which the user may be recommended to clean or replace the multi-fiber connector. When both a low and high standard are employed in the instrument calibration, both offset and a multiplicative correction terms may then be applied to compensate for device-to-device variability.

Apart from providing a means of calibrating across manufacturing differences, in many applications the reflectance standards provide a convenient means of quickly verifying proper functioning of the device. In some embodiments, it is recommended to perform a check of device performance with the standards, prior to each usage of the device. A measurement of the reflectance of the standard at the time of manufacture may be stored in the instrument memory. Later measurements on the standard by the user are then compared to the stored value and a pass/fail indication is provided. In some embodiments, if the device fails the reflectance standard check, they are provided with the option of updating the internal calibration.

In many embodiments further calibration steps are used to account for sources of potential interference, such as due to gas bubbles in an aqueous medium containing suspended micro-organisms. The measured or bubble-corrected reflectance signals may further be converted into units of cell concentration, optical density, or like expressions relating to number of particles in a medium, by means of additional calibration steps. Appropriate methods for applying both bubble calibration/correction and particle-specific calibration are provided in U.S. Pat. No. 9,752,974, which are incorporated herein by reference.

Monitoring of Multiple Parallel Vessels (Multiplexing)

By taking advantage of the availability of mass-produced fiber optic components from the telecommunications industry, many embodiments of the present invention are particularly well-suited for monitoring of multiple small-scale vessels in parallel. The small volume (for example, less than 1 mL) required for the measurement allows the sensor to be used on vessels containing very small volumes. For example, accurate measurements have been demonstrated on vessels containing media volumes as low as 10 mL, despite the presence of other objects in the media such as agitators, sparge tubes, liquid handling tubes, and immersed sensors. The use of fiber optics provides a ready means of distributing and collecting the light across multiple devices without necessitating the use of separate sources and detectors for each application. In some embodiments fiber optic switchers or splitters are used to distribute and/or gather the light to the multiple vessels. The use of mass-produced small multi-fiber connectors as the sensors in many embodiments makes the presently described devices both economical and reliable on multiple parallel vessels. Embodiments in which the vessel adapter is simply attached to the vessel with an adhesive make set-up quick and reliable, while requiring little space on the vessel or in the surrounding environment. Embodiments employing push-pull connectors, such as MPO connectors and receptacles, make it possible to attach or detach the sensor in a single motion. This provides the user with the ability to quickly check that the sensor is working properly, even, for example, during the middle a fermentation run, without risking contamination of the culture. When working with many vessels in parallel (e.g. 4, 12, 24, or more), the advantages of the invention become most evident.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1—Adaption of an MPO for Particle Detection

An example sensor was constructed using an off-the-shelf mass-produced MPO fiber connector and receptacle. The MPO series of connectors and receptacles were originally designed for use in the telecommunications industry, for the purpose of making reproducible and low-loss fiber-to-fiber and fiber-to-component connections for multiple fibers with a single connection. The design and performance of the connectors and receptacles is specified by telecommunications industry standards, such as IEC 61754-7-1, First edition, 2014—"Fibre optic interconnecting devices and passive components—Fibre optic connector interfaces—Part 7-1: Type MPO connector family—One fibre row". The adherence to such standards allows connectors and receptacles from multiple manufacturers to be used interchangeably. The standardization, wide adoption for telecommunications, and competition between multiple manufacturing sources, results in the availability of low-cost and reliable parts. Adaptation of these parts to purposes to which they were not originally designed, such as particle sensing, allows these other applications to take advantage of the low cost and reliability of the parts, without necessarily having an equally large market size for the alternate applications.

Figure 8:
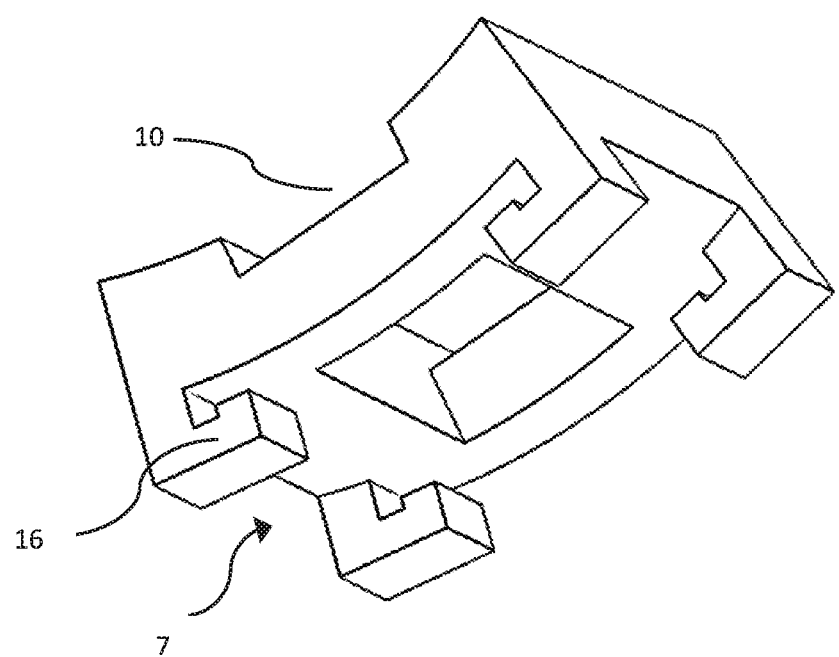
FIG. 8 depicts a vessel adapter design of the present invention used in experiments described in Example 1.

In this example, MPO connectors and receptacles originally designed to make reliable fiber-to-fiber or fiber-to-component connections, were adapted to instead create a sensor for determining the concentration of yeast cell biomass suspended in aqueous solution. A vessel adapter 7, as depicted in FIG. 8 was custom-designed according to the present invention to capture a standard MPO receptacle in an orientation that urges the MPO connector against the side of a vessel, once connected. Hooks 16 on the rear of the vessel adapter provide a means of securely attaching the vessel adapter to the vessel using one or more elastic straps. The cavity 10 in the vessel adapter (depicted in FIG. 8) is designed to accommodate an MPO receptacle. In this example, the MPO receptacle is half of an adapter (Part Number MTP-ADPT, manufactured by Fibertronics) originally designed to allow two MPO connectors to be mated together (for a fiber-to-fiber connector).

The MPO "sensor" was an off-the-shelf multi-mode (MM) "MTP" connector that holds 12 fibers in a single row, with a center-to-center spacing of 250 µm, such as depicted in FIG. 1A. The fiber type was 105/125 µm core/cladding with 0.22 numerical aperture. The MPO connector includes a spring mechanism in its push-pull connector 4 that is normally used to force the fibers in the connector into intimate contact with other fibers (in a fiber-to-fiber adapter) or to opto-electronic components (such as in a laser-to-fiber or detector-to-fiber receptacle) when the connector is plugged into a receptacle. The push-pull mechanism allows the connector to be reproducibly mounted into a receptacle simply by pushing the connector into the receptacle until it latches. The connection is securely maintained under spring force, with low fiber-to-fiber loss (e.g. 0.2 dB or less) and high reproducibility across connections. Disconnection of the connector from the receptacle is accomplished simply by pulling backwards on the spring-loaded latch 4. In this manner the fiber connection and disconnection is quickly and easily made with high reproducibility and low optical loss.

We do not here claim invention to MPO connectors and fittings. However, we find them readily and coincidentally adaptable to solve the different problems of introducing interrogation illumination to particles in solution, while offering an array of detector receivers having a variety of useful options in offset from the illumination source. Further, the MPOs are available, or readily modified to provide/receive desired light frequencies through desired numerical apertures.

In the present invention, instead of making a fiber-to-fiber or fiber-to-component connection, the MPO connector and receptacle are instead adapted to reproducibly and reliably hold the fibers in the MPO connector against the surface of a vessel under spring force. At the end opposite from the MPO connector, the 12 fibers were separated into individual FC/PC connectors so that they could be connected to a laser source and multiple detectors. Referring to FIG. 1B, the first fiber in the row of 12 fibers was connected to a light source, while the remaining 11 fibers (fibers 2-12) were connected to detectors.

The light source was 30 mW TE-cooled 1330 nm diode laser that was split 16 ways using a fiber optic splitter. The 12 detection channels each used a 1 mm diameter active area InGaAs detector with an optical filter that blocks light below 1250 nm. An electronic control board was used to drive the laser, amplify and digitize the detected signals, process the signals, and provide digital communication with external devices such as a personal computer. A user interface software program using the LabView language (National Instruments) was written to collect the data from the control board.

The vessel used in the experiments was constructed from polycarbonate, with a wall thickness of 2.0 mm. Initially the vessel was filled with 0.9% NaCl in water ("isotonic saline"). A stock solution of 200 g/L yeast in isotonic saline was prepared and added in steps (of 2× the preceding concentration) with a pipettor, to create 16 solutions ranging in concentration from 0, 0.012, 0.0124 . . . 200 g/L. Agitation was accomplished with two Rushton-type impellers held on a rod attached to a variable speed mixer. In this experiment, the mixing speed was held fixed at 500 rpm.

Figure 9A:
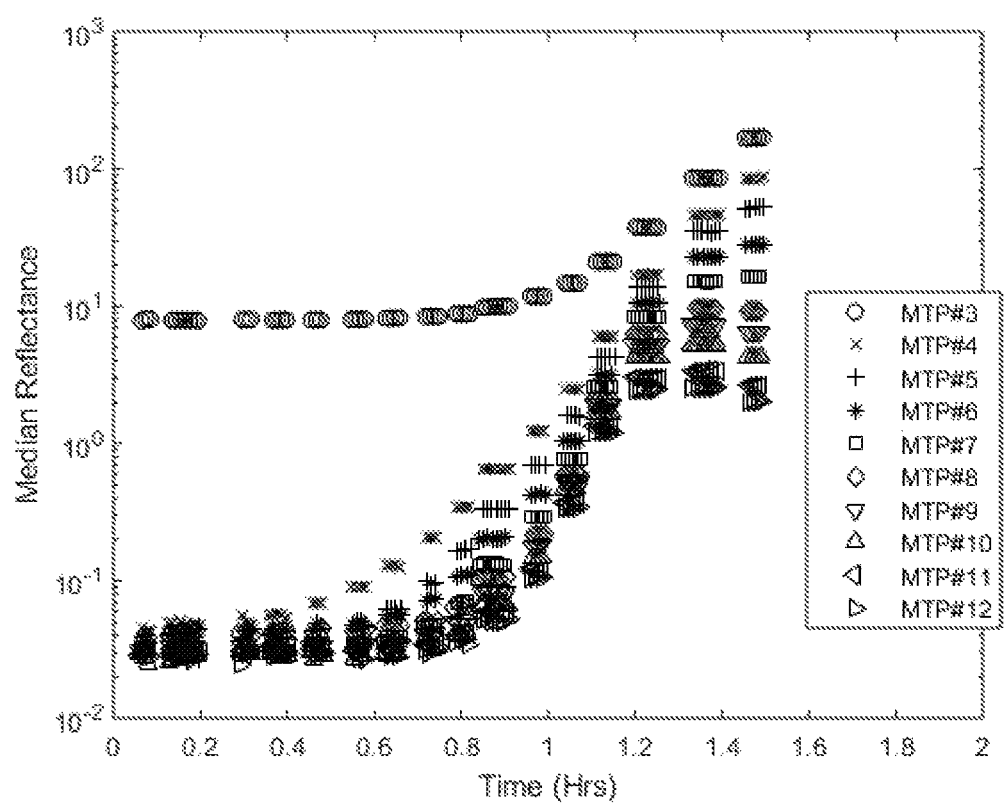
FIG. 9A is a graph of the median reflectance vs time for a sensor of the present invention as yeast is added incrementally to a vessel, as further described in Example 1.
Figure 9B:
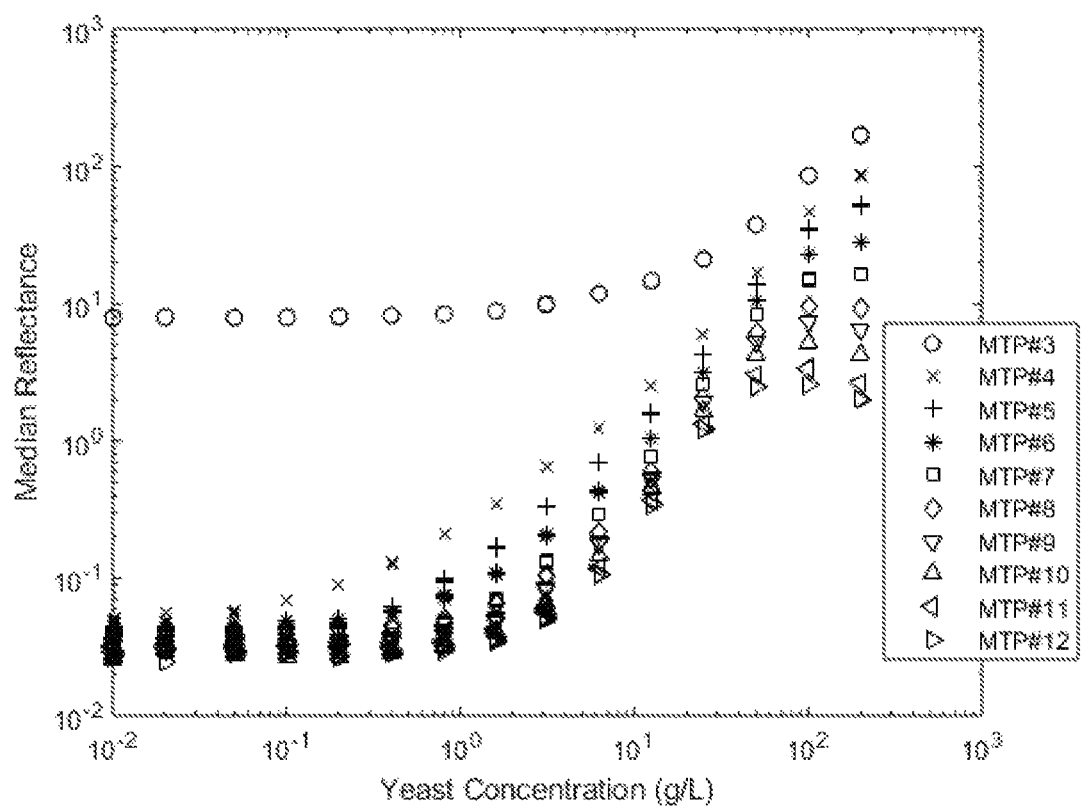
FIG. 9B is a graph of the median reflectance vs yeast concentration for a sensor of the present invention, as further described in Example 1.
Figure 9C:
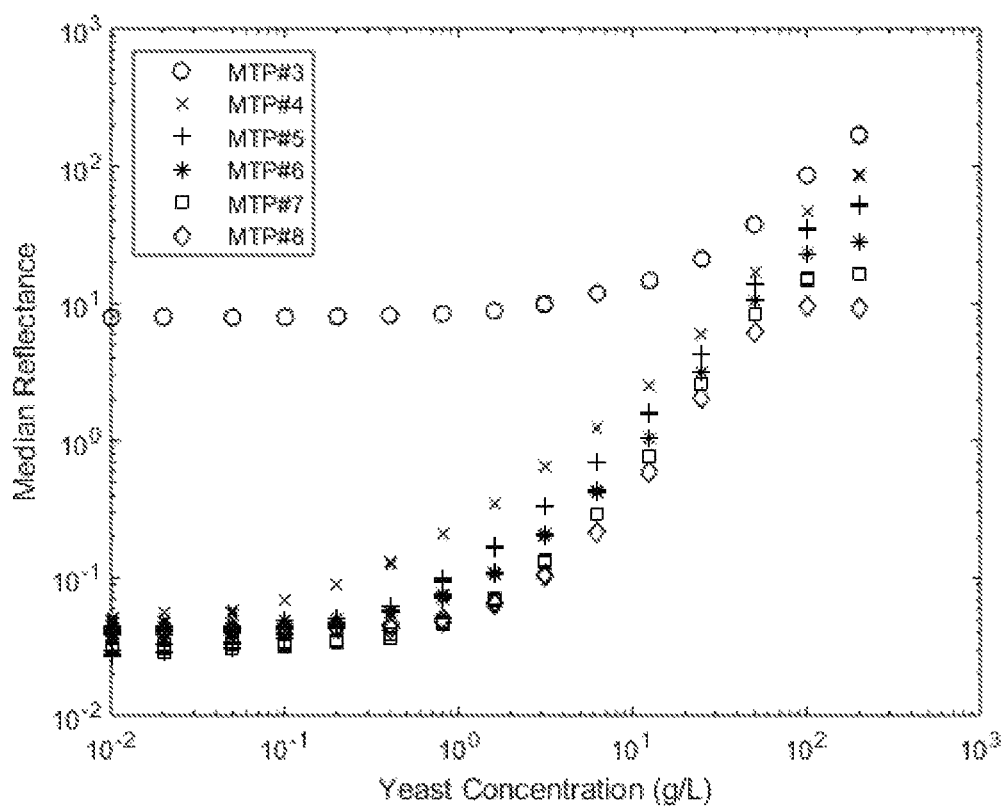
FIG. 9C is a graph showing the same data as in FIG. 9B, but for a reduced set of detection fibers.
Figure 9D:
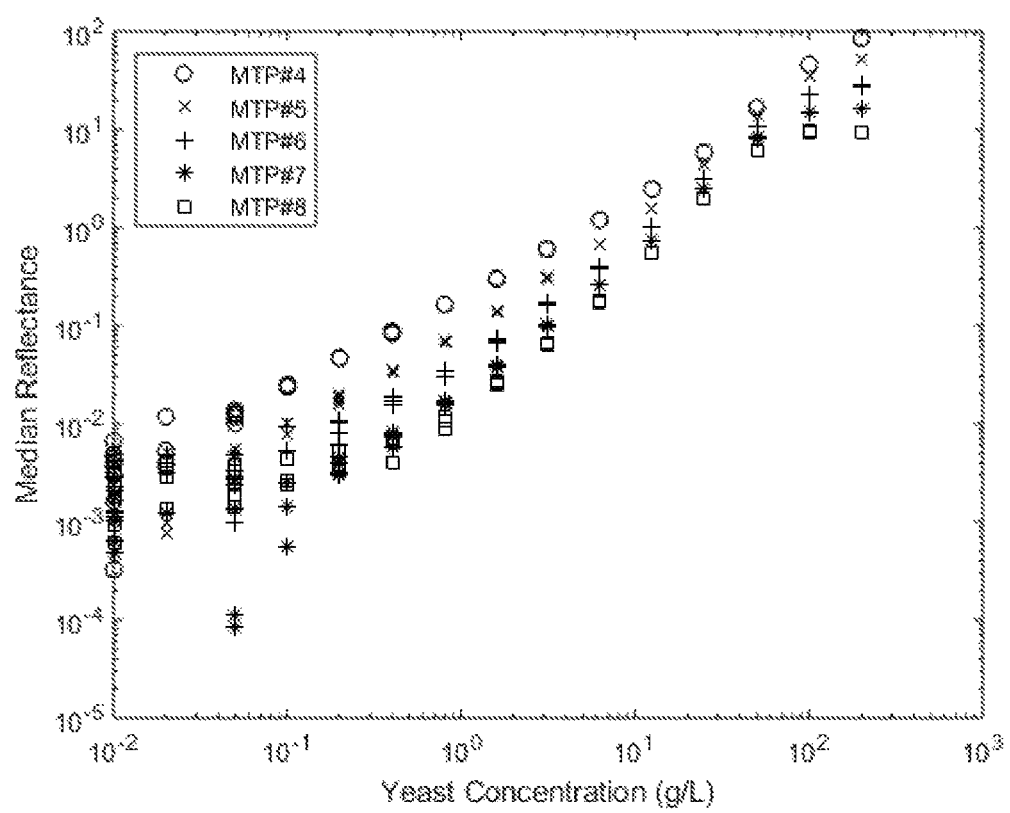
FIG. 9D is a graph of the same data as in FIG. 9C, but for a reduced set of detection fibers, and with the reflectance at zero concentration subtracted from the reflectance at all other concentrations.

A time-course plot of the reflectance measured on each sensor type over all yeast addition steps is provided in FIG. 9A. Each marker (circle, cross, etc) in the figure represents one (2-3 sec) measurement on each sensor type. About 3-10 measurements on each sensor type were collected under each yeast condition. The same reflectance data (without averaging) are plotted as a function of yeast concentration in FIG. 9B. The same plot, but limiting the data only to MTP channels 3-8, is shown in FIG. 9C. The result of offsetting the reflectance for these sensors by the reflectance measured at zero concentration, is shown in FIG. 9D. Table 2 summarizes the reflectance signal levels at baseline (zero concentration) and peak (200 g/L) and the observed low and high concentration limits for monotonic reflectance change.

TABLE 2

Summary of Baseline and Linear Range for Different Sensor Configurations

| Sensor Config. | Baseline Signal | Peak Signal (200 g/L) | Peak/Baseline | Min. Biomass (g/L) | Max. Biomass (g/L) | Biomass Range (Max/Min) |
| --- | --- | --- | --- | --- | --- | --- |
| MTP3 | 7.85 | 169 | 21 | 0.2 | >200 | >1,000 |
| MTP4 | 0.048 | 86 | 1,790 | 0.1 | >200 | >2,000 |
| MTP5 | 0.029 | 52.1 | 1,800 | 0.1 | 200 | 2,000 |
| MTP6 | 0.043 | 28.1 | 653 | 0.4 | 100 | 250 |
| MTP7 | 0.031 | 16.3 | 526 | 0.4 | 50 | 120 |
| MTP8 | 0.042 | 9.24 | 220 | 0.8 | 50 | 60 |
| MTP9 | 0.033 | 6.47 | 196 | 1.6 | 50 | 30 |
| MTP10 | 0.028 | 4.27 | 152 | 1.6 | 25 | 15 |
| MTP11 | 0.032 | 2.66 | 83 | 1.6 | 25 | 15 |
| MTP12 | 0.027 | 2.02 | 75 | 3.2 | 25 | 8 |

The sensor configurations providing the widest range of sensitivity to biomass were MTP4 and 5, corresponded to source-detector separation in the range of 0.75 to 1.0 mm. This source-detector separation is in good agreement with a computer simulation, which predicts that a source-detector separation of 0.83 mm should be optimal for a wall thickness of 2.0 mm (see Table 1). At shorter source-detector separations (e.g. MTP3) the baseline signal increases, due to signal contribution of specular reflections from the vessel wall. At longer source-detector separations (e.g. MTP 6 and higher) the overall signal level decreases, leading to reduced sensitivity at low biomass, and the maximum resolvable biomass decreases, because the signal has a tendency to roll-over (i.e., not increase monotonically) with increasing biomass. In summary, the optimal source-detector separation is selected by balancing the trade-off between over-sensitivity to specular reflections (e.g. when the source-detector separation is too small) and under-sensitivity to changes in biomass concentration (e.g. when the source-detector separation is too large). The optimal choice of source-detector separation will therefore depend on the thickness of the vessel wall.

Figure 4A:
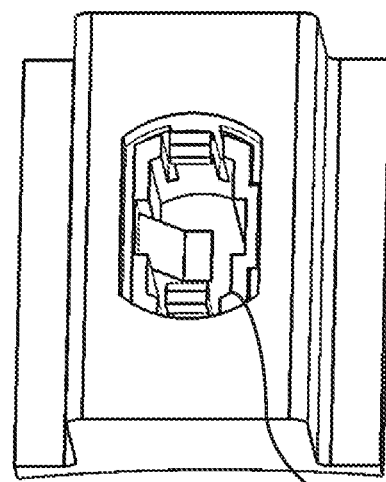
FIGS. 4 A-C depict different perspective views of an example adapter of the present invention for attaching a multi-fiber connector to a vessel, which comprises a standard connector adapter for multi-fiber connectors held within a vessel adapter of the present invention for holding the connector against a vessel. The top left view 4A is depicted from the side of the adapter into which the multi-fiber connection is made. The bottom view 4C is depicted from the side of the adapter that attaches to the vessel.
Figure 4B:
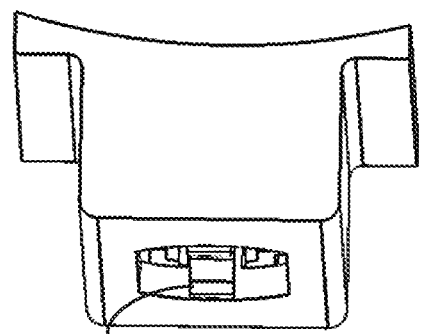
Figure 4C:
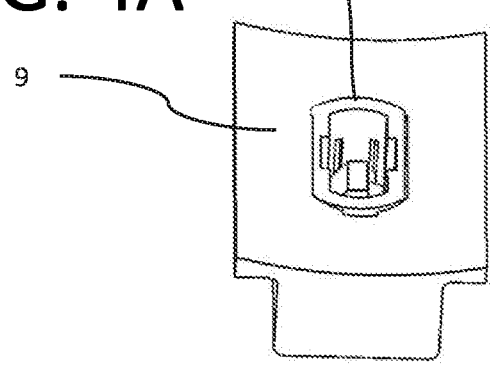
Figure 5A:
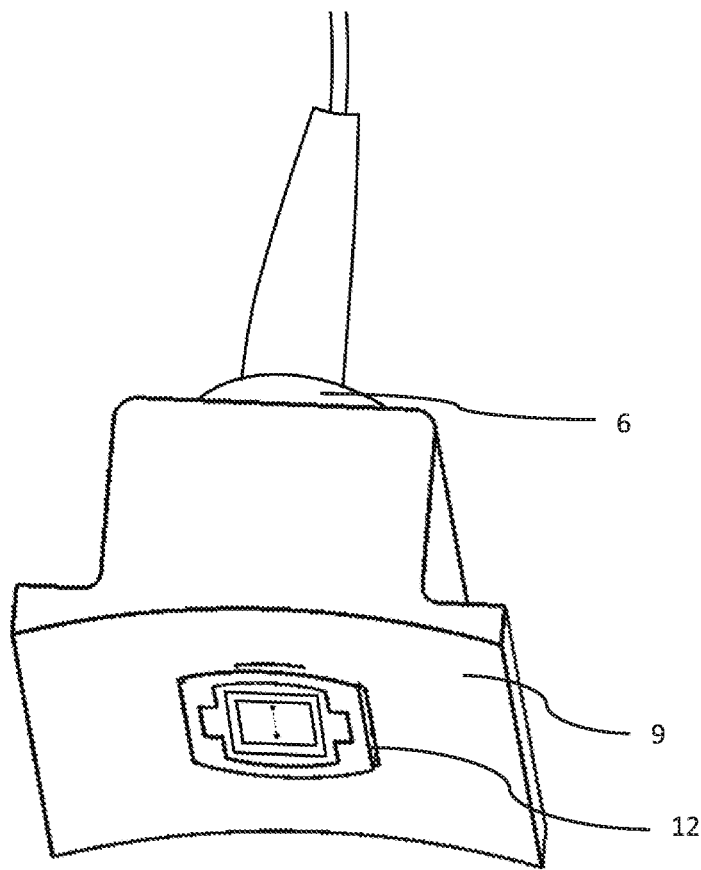
FIGS. 5A and 5B depict two different perspective views of an example adapter of the present invention for attaching a multi-fiber connector to a vessel, in which a multi-fiber receptacle has been mated into the adapter.
Figure 5B:
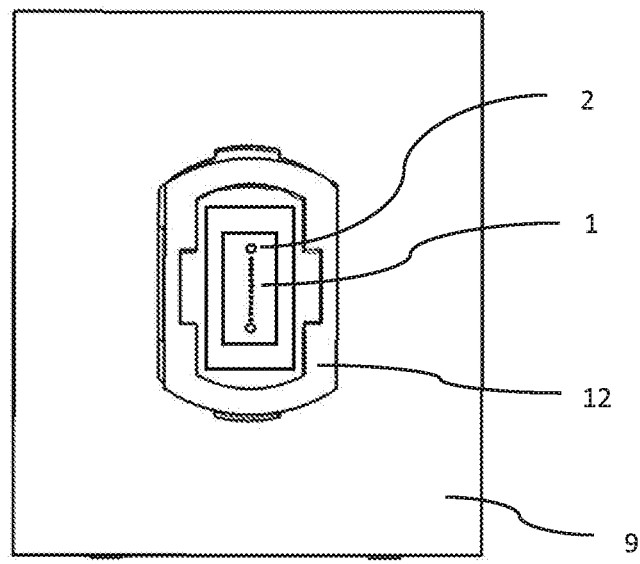

Example 2—Multiple Sensors Calibrated for Biomass Measurement with Reduced Bubble Interference A second example of the present invention is provided by a series of experiments on a clear plastic polycarbonate vessel with about 300 mL capacity. In this example the vessel adapter was 3D printed (Proto Labs Inc, material: PA 12 black multi Jet Fusion), based on the design depicted in FIG. 3B. An off-the-shelf MPO adapter (Amphenol part number 955-120-5110) was disassembled and the interior MPO receptacle portion was bonded to the vessel adapter using an adhesive (Loctite part number 401). The resulting assembly is depicted in FIGS. 4A-C. This vessel adapter assembly was fixed to the vessel using two-sided adhesive tape (part number VHB 5925, manufactured by 3M), obviating the need for hooks or a strapping mechanism. The cable break-out at the opposite end of the cable from the MPO connector was a duplex LC connector, with fiber #1 connected to the source laser and fiber #4 to the detector (refer to FIG. 1B for fiber numbering). The vessel adapter with an MPO connector and cable plugged into it is depicted in FIGS. 5A-B. Two such assemblies ("sensors") were placed on the same vessel to provide simultaneous measurements.

Figure 10A:
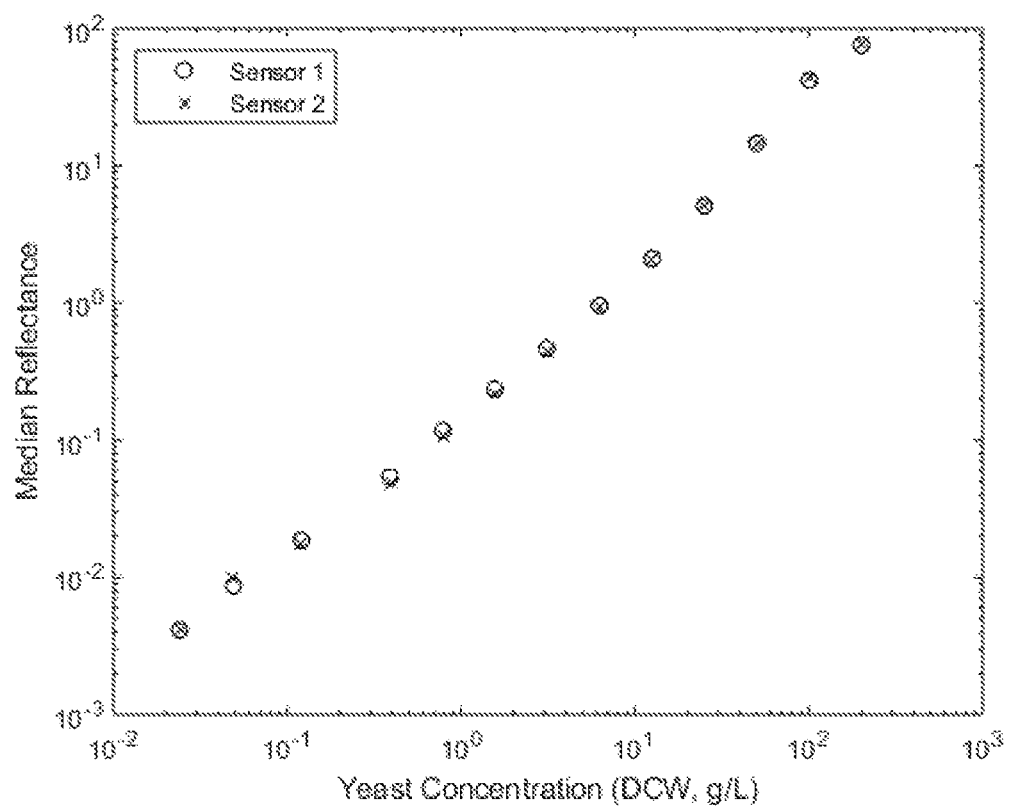
FIG. 10A is a graph showing the calibrated response as a function of yeast concentration of two sensors of the present invention on the same vessel, as further described in Example 2.
Figure 10B:
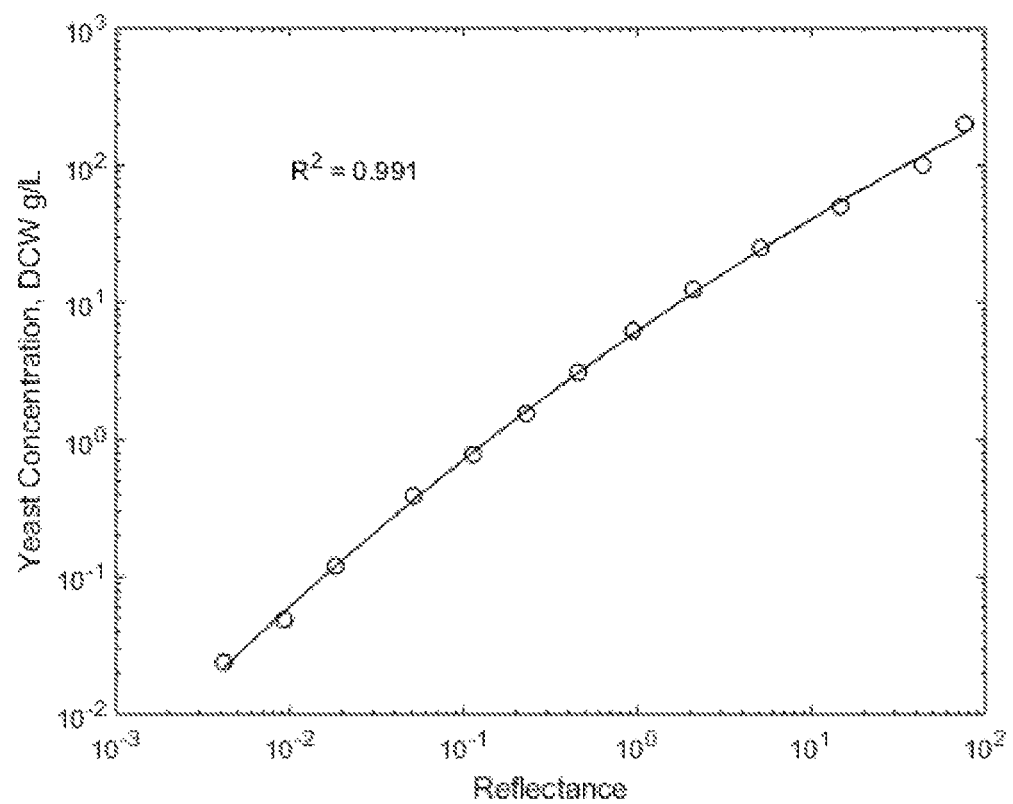
FIG. 10B is a graph showing a calibration curve for yeast concentration vs. reflectance for a sensor of the present invention, as further described in Example 2.

As in Example 1, a wide range of yeast concentrations was created by adding a stock solution of 200 g/L yeast in steps to the vessel, initially filled with isotonic saline. The response of the two sensors was calibrated using two reflectance points: a low (water) reflectance and a high reflectance (12.5 g/L yeast dry cell weight). The calibrated sensor responses to changes in yeast concentration are shown overlaid in FIG. 10A. After calibration, the two sensors were in close agreement and able to resolve changes in yeast concentration across a range of yeast concentrations from about 0.025 to 200 g/L. The sensors were further calibrated to report directly in yeast concentration (g/L dry cell weight) by fitting the known yeast concentration versus the measured sensor reflectance to a 3rd order polynomial, as shown in FIG. 10B. The $R^2$ correlation coefficient and root mean squared error from the fit were 0.991 and 8.9% respectively.

A bubble calibration map was generated for the sensor following the methods described in U.S. Pat. No. 9,752,974, which are incorporated herein by reference. Additional experiments were performed in which the agitation (4 levels, 750-2000 rpm) and sparge rate (room air, 4 levels, 0-2 vvm) were varied over a range of yeast concentrations (9 logarithmically spaced levels, 0.01-200 g/L). With the bubble calibration applied, the root mean squared error induced by changes in bubbling and agitation was less than 15% for yeast concentrations above 0.1 g/L and less than 5% for yeast concentrations above 0.5 g/L.

Example 3—Alternate Optical Fiber Arrangement and Adaptation for Biomass Monitoring Through the Optical Port of a Single Use Fermentor A third example of the present invention involves the use of a multi-fiber connector and adapter to measure biomass through an optical port built into the side of a single use fermentor bag. Unlike the first two examples, which employed off-the-shelf MPO-type connectors with fibers arranged linearly and oriented along the long axis of a cylindrical vessel surface, in the present example the multi-fiber connector employs a non-linear arrangement of fibers designed for measurement through a flat window. The fiber arrangement 1, depicted in FIG. 12A, includes two different fiber types, one with 500 μm outer diameter, and a second with 240 μm outer diameter, that are close-packed within a single aperture having a diameter of 1.1 mm, within the multi-fiber connector 6. In the present example, two of the fibers with 240 μm outer diameter are selected as the source and detector fibers, while the remaining fibers provide structural support, maintaining the desired separation between the source and detector fibers of 0.72 mm (center-to-center). This source-detector separation was determined based on optical modeling (see Selection of the Source-Detector Separation, above), to be ideal for a polycarbonate window 26 thickness of about 1 mm, as was the case for the optical port 27 of the single use fermentor that was tested in this example.

In this example, the multi-fiber connector was custom machined out of polyether ether ketone (PEEK). For larger numbers of parts (e.g. production volumes) this part could be produced by injection molding, with attendant cost savings. An alternate version of the multi-fiber connector was constructed by drilling separate apertures (240 μm diameter) for the source and detector fibers. However, in practice the fabrication of this part was expensive and difficult to reproduce due to the small size of the holes. The design depicted at the top of FIG. 12 has the advantage that only a single large aperture is required, and the fibers themselves are used to maintain the separation between the source and detector fibers. This results in the benefit of reduced cost and improved reproducibility of the separation between the source and detector fibers.

The position of the fibers within the multi-fiber connector 6 was fixed using epoxy (Epo-tek part number 353ND), after which the face of the multi-fiber connector was polished, using standard fiber optic polishing techniques. Only the two optically active (source and detector) fibers were extended for the length of the cable; the remaining fibers were terminated at the end of the multi-fiber connector, thereby saving on materials cost, reducing the cable weight, and increasing the cable flexibility. The two reduced diameter sections depicted on the right (rear) side of the multi-fiber connector 6 in FIG. 12A provide attachment points for inner and outer layers of cable jacketing, which help to protect the fibers from harsh environments and accidental breakage.

Figure 12B:
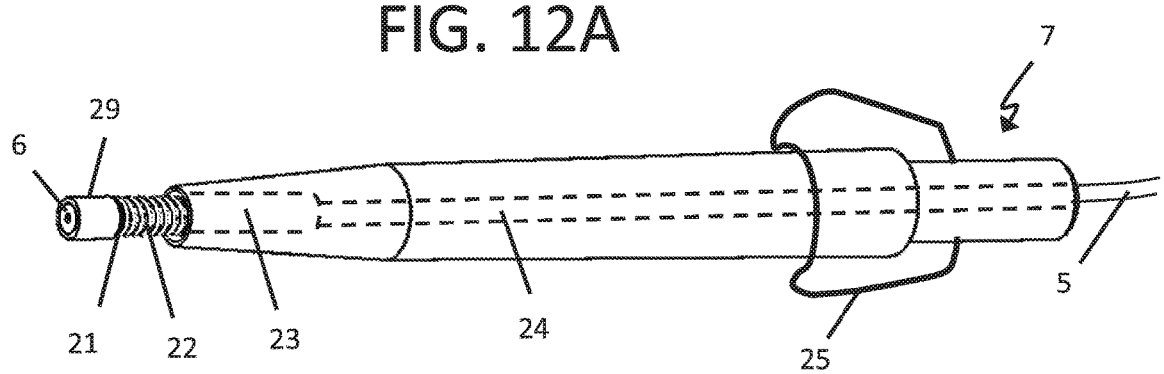

The multi-fiber connector 6 with attached cable 5, is shown integrated into a vessel adapter 7 in FIG. 12B. The vessel adapter 7 contains an aperture 24 that serves as a receptacle for the multi-fiber connector 6, allowing it to be threaded through the interior of the vessel adapter. The multi-fiber connector is also threaded through a spring 22, at the tip of the adapter. The front stop for the spring is provided by attaching a retaining ring 21 to the back side of the multi-fiber connector 6. A back-stop for the spring is provided by the spring cavity 23 built into the vessel adapter 7. An outer ferrule ring 29 is optionally fitted over the tip of the multi-fiber connector 6 in order to increase its effective diameter to more closely match the inner diameter of the optical port 27 just behind the optical window 26, when the multi-fiber connector 6 and vessel adapter 7 are inserted into the optical port. By matching the effective outer diameter of the multi-fiber connector to the inner diameter of the optical window, the reproducibility of the positioning and parallelism of the face of the multi-fiber connector relative to the face of the optical window may be improved.

Figure 12C:
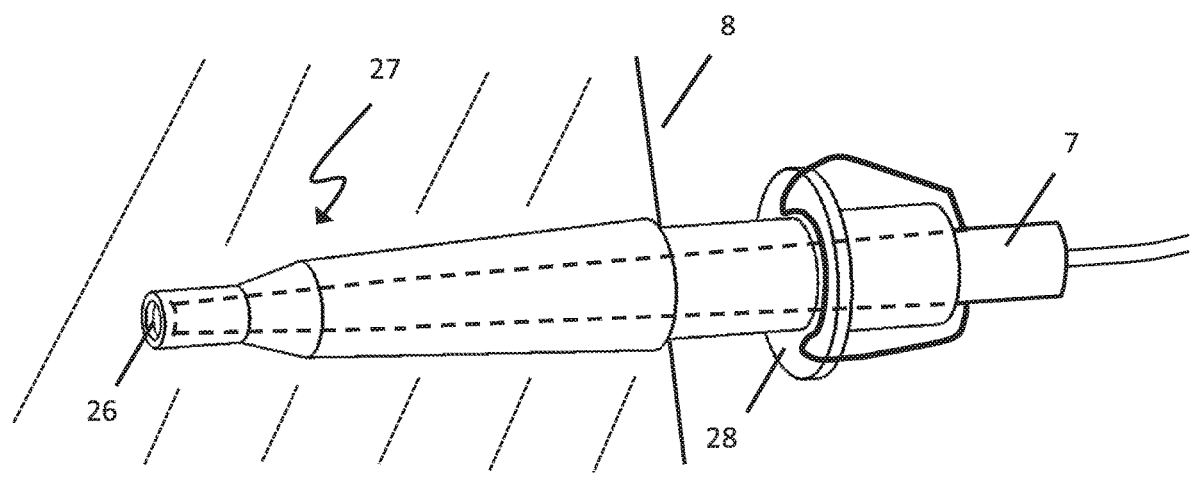

An optical port 27 in a single use fermentor is depicted in FIG. 12C, with the vessel adapter 7 and multi-fiber connector 6 assembly (as depicted in FIG. 12B) inserted into it. The optical port is embedded into a flexible plastic wall 8 of a single use fermentor. The interior space (containing media) of the fermentor is depicted by dashed diagonal lines in FIG. 12C. As the vessel adapter 7 and multi-fiber connector 6 assembly is inserted into the optical port 27, the face of the multi-fiber connector 6 is compressed against the optical window 26, under spring 22 force. When the spring 22 has been sufficiently compressed, a latch 25 provided on the vessel adapter 7 is rotated over a ring 28 on the optical port 27, thereby fixing the multi-fiber connector 6 against the inside of the optical window 26. The latch 25 is shaped so that a small extension of its shape is required in order to reach over the outer diameter of the ring 28, which is at least partially relaxed once the latch is further urged towards the center of the optical port. In this manner the latch is maintained under force in an engaged position until a user intentionally disengages it. In one embodiment the latch is constructed by bending stainless steel wire. Holes in the vessel adapter 7 are provided so that the latch can be inserted and maintained within the holes under spring force.

The opto-electronic components, control board, and software interface were as described in Example 1, above, except that a 5 mW laser was employed and a fiber optic splitter was not employed before coupling it into the source fiber. A bubble correction map and yeast (*Saccharomyces cerevisiae*) biomass calibration were developed in the same manner as described in Examples 1 and 2, but specific to the optical configuration of this example. In order to test the sensitivity of the calibrated instrument across changes in process conditions, a single use fermentor was filled with yeast suspended in isotonic saline at 6 concentrations (dry cell weight): 0.2, 0.8, 3.2, 12.5, 50, and 200 g/L. At each yeast concentration four different process conditions (agitation rates and gas sparge rates) were tested, representing a range typical of an aerobic microbial fermentation: (1) 750 rpm, 0 vvm; (2) 1500 rpm, 0.5 vvm; (3) 1750 rpm, 1.0 vvm; and (4) 2000 rpm, 2.0 vvm. Agitation was performed with a dual Rushton-type impeller. Sparging was performed using compressed room air delivered through a micro-frit; the vvm units represent volume of gas per minute per volume of media in the fermentor.

Figure 13:
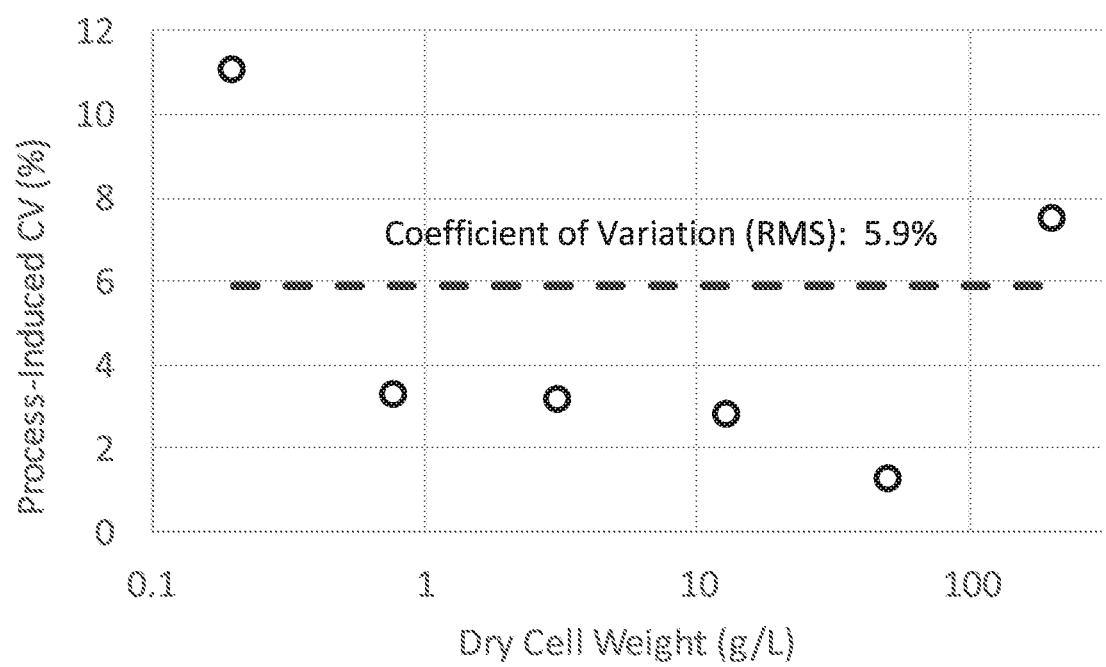
FIG. 13 is a graph of the process-induced coefficient of variation of optically predicted biomass (dry cell weight) across a wide range of process conditions, as further described in Example 3.

The coefficient of variation (CV) of the optically predicted yeast dry cell weight across the four tested process conditions was computed at each yeast concentration, with the results summarized in FIG. 13. Overall (root mean squared across all concentrations), the CV was 5.9%, indicating that high biomass prediction accuracy was maintained despite the wide range of process conditions that were tested.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations and permutations, all of which cannot reasonably be recited individually in this document, but can be understood by one of skill in the art on review of this specification.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A device for non-invasively determining the concentration of particles in a medium within a vessel, which device comprises:
   a multi-fiber connector attached to a fiber optic cable;
   a light source optically coupled into one or more optic fibers, the one or more optic fibers housed in the fiber optic cable;
   a detector optically coupled to one or more of the optic fibers, the one or more optic fibers housed in the fiber optic cable;
   an adapter comprising a receptacle for the multi-fiber connector and a mount configured to attach the adapter to the vessel so that light from the light source is directed by a first optical fiber into the medium, scattered by the particles, and a portion of the scattered light is collected by a second optical fiber connected to the detector which generates a signal; and,
   a processor configured to receive and to correlate the signal to the concentration of particles in the medium.

2. The device of claim 1, wherein the multi-fiber connector is a push on type connector, for which secure connection with the receptacle requires only pushing the connector into the receptacle.

3. The device of claim 1, wherein the multi-fiber connector comprises at least two optical fibers arranged along a line on the face of the connector, and the adapter is configured so that said line is parallel to a non-curved dimension of the vessel.

4. The device of claim 1, wherein the separation between the fibers to which the light source and detector are connected is selected according to the thickness of the vessel wall.

5. The device of claim 4, wherein the separation between the light source and detector fibers is selected to minimize sensitivity to specular reflections from the vessel wall while maximizing the range of sensitivity to particle concentrations.

6. The device of claim 1, wherein the multi-fiber connector is an MPO connector.

7. The device of claim 1, wherein the particle being measured is a biological cell and the primary constituent of the medium is water.

8. The device of claim 7, wherein the light source emits in the near infrared spectral region where water absorbance is strong enough to limit the mean path length of light into the medium to less than 5 cm, even in the substantial absence of biological cells.

9. The device of claim 1, further comprising at least one reflectance standard, wherein the multi-fiber connector is attached to the reflectance standard, thereby providing a means of calibrating or verifying the performance of the device.

10. The device of claim 1, wherein the connector comprises a keying feature and the receptacle comprises a channel feature that mates with the keying feature, thereby providing a means of maintaining a fixed orientation between the connector and receptacle across repeated insertions of the connector into the receptacle.

11. The device of claim 1, wherein the receptacle comprises one or more latches that capture and hold in place the connector, when the connector has been pressed into the receptacle past a defined depth.

12. The device of claim 1, wherein the surface of the adapter that is attached to the vessel is curved in the same plane as the vessel surface to which it is attached.

13. The device of claim 1 wherein the vessel is a single use fermentor.

14. The device of claim 13 wherein an optical port is provided on the fermentor, which is used as the point of attachment for the adapter.

15. The device of claim 14 wherein the adapter comprises a latch which secures the multi-fiber connector against a window within the optical port.

16. The device of claim 1 wherein the multi-fiber connector comprises a ferrule with one or more cavities accommodating a plurality of optical fibers in a fixed arrangement.

17. A non-invasive method for measuring biomass in a bioreactor, the method comprising:
   providing a device for non-invasively determining the concentration of particles in a medium within a vessel, which device comprises:
      a multi-fiber connector attached to a fiber optic cable;
      a light source optically coupled into one or more optic fibers, the one or more optical fibers housed in the fiber optic cable;

a detector optically coupled to one or more of the optic fibers, the one or more optical fibers housed in the fiber optic cable;

an adapter comprising a receptacle for the multi-fiber connector and a mount configured to attach the adapter to the vessel so that light from the light source is directed by a first optical fiber into the medium, scattered by the particles, and a portion of the scattered light is collected by a second optical fiber connected to the detector which generates a signal; and, a processor configured to receive and to correlate the signal to the concentration of particles in the medium;

attaching the multi-fiber connector to an exterior surface of the bioreactor using the adapter;

measuring the intensity of the source light directed into the bioreactor through the multi-fiber connector, scattered by the biomass, and collected through the multi-fiber connector onto the one or more detectors; and, correlating the measured light intensity to the biomass in the bioreactor.

18. The method of claim 17, wherein the exterior surface of the bioreactor to which the multi-fiber connector is attached is a port built into the bioreactor.

19. The method of claim 17, further comprising selecting a separation between the source and detector fibers at a face of the multi-fiber connector according to a thickness of the exterior surface of the bioreactor to which the multi-fiber connector is attached.

20. The method of claim 17, wherein the bioreactor comprises a disposable fermentor bag.

\* \* \* \* \*

UNITED STATES PATENT AND TRADEMARK OFFICE
CERTIFICATE OF CORRECTION

| | | |
|---|---|---|
| PATENT NO. | : 10,989,645 B2 | Page 1 of 1 |
| APPLICATION NO. | : 16/537555 | |
| DATED | : April 27, 2021 | |
| INVENTOR(S) | : Gerald P. Coleman et al. | |

It is certified that error appears in the above-identified patent and that said Letters Patent is hereby corrected as shown below:

On the Title Page

Item [71], Replace "INSTRUMNETS" with --INSTRUMENTS--.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*